US012649749B2

(12) United States Patent
Gu et al.

(10) Patent No.: US 12,649,749 B2
(45) Date of Patent: Jun. 9, 2026

(54) PREPARATION AND APPLICATION OF TRICYCLIC PYRIMIDINONE COMPOUND AND ITS COMPOSITION

(71) Applicant: NEUSCO BIOTECH LIMITED, Shanghai (CN)

(72) Inventors: Zhenghua Gu, Shanghai (CN); Dongqin Wang, Shanghai (CN); Youhong Hu, Shanghai (CN)

(73) Assignee: NEUSCO BIOTECH LIMITED, Shanghai (CN)

( * ) Notice: Subject to any disclaimer, the term of this patent is extended or adjusted under 35 U.S.C. 154(b) by 628 days.

(21) Appl. No.: 18/004,922

(22) PCT Filed: Jul. 6, 2021

(86) PCT No.: PCT/CN2021/104826

§ 371 (c)(1),
(2) Date: Jan. 10, 2023

(87) PCT Pub. No.: WO2022/007810

PCT Pub. Date: Jan. 13, 2022

(65) Prior Publication Data

US 2023/0357268 A1 Nov. 9, 2023

(30) Foreign Application Priority Data

Jul. 10, 2020 (CN) ......................... 202010661516.6

(51) Int. Cl.

| | |
|---|---|
| ***C07D 487/04*** | (2006.01) |
| ***A61K 31/519*** | (2006.01) |
| ***A61P 9/10*** | (2006.01) |
| ***A61P 13/08*** | (2006.01) |
| ***A61P 25/28*** | (2006.01) |
| ***A61P 27/02*** | (2006.01) |
| ***A61P 27/06*** | (2006.01) |
| ***C07D 471/14*** | (2006.01) |
| ***C07D 498/14*** | (2006.01) |
| ***C07D 513/12*** | (2006.01) |

(52) U.S. Cl.

CPC .................................. *C07D 498/14* (2013.01)

(58) Field of Classification Search

CPC .. C07D 487/04; C07D 498/14; C07D 513/12; C07D 471/14; A61K 31/519; A61P 25/28; A61P 27/02; A61P 27/06; A61P 13/08; A61P 9/10

See application file for complete search history.

(56) References Cited

U.S. PATENT DOCUMENTS 10,125,141 B2 11/2018 Wan et al.

FOREIGN PATENT DOCUMENTS

| | | | |
|---|---|---|---|
| CN | 106536525 | A | 3/2017 |
| WO | 2012037782 | A1 | 3/2012 |
| WO | 2013014185 | A1 | 1/2013 |
| WO | 2014114694 | A1 | 7/2014 |
| WO | 2016010927 | A1 | 1/2016 |
| WO | 2016011930 | A1 | 1/2016 |
| WO | 2016012916 | A1 | 1/2016 |

OTHER PUBLICATIONS

International Search Report issued in International Application No. PCT/CN2021/104826; mailed Sep. 29, 2021; 7 pgs.

Written Opinion issued in International Application No. PCT/CN2021/104826; mailed Sep. 29, 2021; 8 pgs.

Extended European Search Report in Corresponding European Application No. 21838236.4, dated Jul. 2, 2024; 7 pgs.

First Examination Report in Corresponding Australian Application No. 2021304763, dated Oct. 19, 2023; 4 pgs.

First Office Action in Corresponding Chinese Application No. 202010661516.6, dated May 31, 2023; 22 pgs.

First Office Action in Corresponding Russian Application No. 2023100349/04, dated Oct. 26, 2023; 22 pgs.

Invitation to Respond to Written Opinion in Corresponding Singapore Application No. 11202300181X, dated Jun. 16, 2025; 10 pgs.

Notice of Reasons for Refusal in Corresponding Japanese Patent Application No. 2022-580773, mailed Mar. 12, 2024; 9 pgs.

Notice of Reasons for Rejection in Corresponding Korean Application No. 10-2023-7003368, mailed May 13, 2025; 11 pgs.

Second Examination Report in Corresponding Australian Application No. 2021304763, dated Apr. 4, 2024; 3 pgs.

Second Office Action in Corresponding Russian Application No. 2023100349/04, dated Mar. 6, 2024; 10 pgs.

Third Office Action in Corresponding Russian Application No. 2023100349/04, dated Jun. 28, 2024; 8 pgs.

*Primary Examiner* — Bruck Kifle

(74) *Attorney, Agent, or Firm* — HAUPTMAN HAM, LLP

(57) ABSTRACT

Disclosed is a tricyclic pyrimidinone compound of Formula (I) or a pharmaceutically acceptable salt thereof, which is a novel Lp-PLA2 inhibitor useful in treating neurodegeneration-related diseases such as Alzheimer's disease (AD), glaucoma and age-related macular degeneration (AMD), or cardiovascular diseases including atherosclerosis.

11 Claims, No Drawings

PREPARATION AND APPLICATION OF TRICYCLIC PYRIMIDINONE COMPOUND AND ITS COMPOSITION

RELATED APPLICATIONS

The present application is a U.S. National Phase of International Application Number PCT/CN2021/104826 filed Jul. 6, 2021 and claims priority to Chinese Application Number 202010661516.6 filed Jul. 10, 2020.

TECHNICAL FIELD

The invention belongs to the field of medicine, and in particular relates to a tricyclic pyrimidinone compound, its tautomer, mesomer, racemate, enantiomer, diastereoisomer, or mixture thereof forms, its preparation method, its medicinal composition, and its use in medicine. In particular, the present disclosure relates to tricyclic pyrimidinone derivatives represented by general formula (I), their preparation methods and pharmaceutical compositions containing the derivatives, and their use as LpPLA2 inhibitors for the treatment of neurodegenerative related diseases, such as Alzheimer's disease (AD), glaucoma and age-related macular degeneration (AMD), or atherosclerosis, diabetic macular edema.

BACKGROUND

Lipoprotein-associated phospholipase A2 (Lp-PLA2) is a member of the phospholipase A2 superfamily (Dennis E A, Cao J, Hsu Y H, Magrioti V, Kokotos G. *Chem Rev.* 2011, 111, 6130-6185). It is mainly secreted by monocytes, macrophages, T lymphocytes and chief cells (Stafforini D M, Elstad M R, McIntyre T M, Zimmerman G A, Prescott S M. J Biol Chem. 1990, 265: 9682-9687; Nakajima K, Murakami M, Yanoshita R, Samejima Y, Karasawa K, Setaka M, Nojima S Kudo I. J Biol Chem. 1997, 272, 19708-19713). Phosphatidylcholine sn-2 esters are produced during the oxidation of low-density lipoprotein (LDL). Lp-PLA2 is responsible for the hydrolysis of oxidized phosphatidylcholine sn-2 ester, which then produces oxidized fatty acids and lysophosphatidylcholine (LysoPC) (Caslake M J, Packard C J, Suckling K E, Holmes S D, Chamberlain P, Macphee C H. Atherosclerosis. 2000, 150, 413-419; MacPhee C H, Moores K E, Boyd H F, Dhanak D, Ife R J, Leach C A, Leake D S, Milliner K J, Patterson R A, Suckling K E, Tew D G, Hickey D M. Biochem J. 1999, 338, 479-487). Both oxidized fatty acids and LysoPC play roles in activating macrophages, increasing oxidative stress, affecting the function of T lymphocytes, and inducing inflammatory responses (Quinn M T, Parthasarathy S, Steinberg D. Proc Natl Acad Sci USA. 1988, 85, 2805-2809). LysoPCs have been reported to induce the release of multiple cytotoxic inflammatory cytokines (Shi, et al, Atherosclerosis, 2007, 191, 54-62). In addition, LysoPCs have also been involved in the activation of leukocytes, the induction of apoptosis, and the mediation of endothelial dysfunction (Wilensky et al, Current Opinion in Lipidology, 2009, 20, 415-420).

It has been reported that plasma level of Lp-PLA2 is associated with cardiovascular diseases (Fitzpatrick A L, Irizarry M C, Cushman M, Jenny N S, Chi G C, Koro C. *Atherosclerosis.* 2014, 235, 384-391), diabetic macular edema (DME) (Staurenghi G, Ye L, Magee M H, Danis R P, Wurzelmann J, Adamson P, McLaughlin M M, Darapladib D M E S G. *Ophthalmology* 2015, 122, 990-996), and prostate cancer (Bertilsson H, Tessem M B, Flatberg A, Viset T, Gribbestad I, Angelsen A, Halgunset J. *Clin Cancer Res.* 2012, 18, 3261-3269).

Alzheimer's disease (AD) is a chronic neurodegenerative disease that results in decreased cognitive abilities, mood swings, irreversible memory loss, disorientation, speech impairment, and loss of self-protection (Hardy J, et al. *Science* 2002, 297, 353-356). Alzheimer's disease usually starts slowly and gets worse over time, which is the cause of 60% to 70% of dementia cases and affects about 6% of the population over 65 years old. AD patients will gradually withdraw from family and society, rely more and more on help, and eventually progress to death. AD is one of the most costly diseases in developed countries and also with high costs in other countries. These costs will increase dramatically, especially as aging becomes a major societal issue. Needless to say, AD is a complex disease involving multiple factors. Although the etiology of AD has not been fully elucidated, it is clear that several factors are involved in the initiation and progression of the disease, including aggregated tau protein and Aβ peptide, oxidative stress, and neuroinflammation (Echeverria V, Yarkov A, Aliev G. *Prog Neurobiol.* 2016, 144, 142-157). The current research and development of AD drug is mainly focused on targets of Aβ amyloidosis and tau (Chiang K, Koo E H. *Annu Rev Pharmacol Toxicol.* 2014, 54, 381-405; Awasthi M, Singh S, Pandey V P, Dwivedi U N. *J Neurol Sci.* 2016, 361, 256-271). However, despite strong preclinical data, results from late-stage clinical trials have so far failed to demonstrate clinical efficacy. These disappointing results suggest that other mechanisms of neuropathology, such as oxidative stress and neuroinflammation, may have to be explored for AD therapy.

Elevated levels of Lp-PLA2 in plasma increase the risk of dementia, including AD (Van Oijen, et al. Annals of Neurology, 2006, 59, 139). In addition to vascular dementia and mixed dementia, high oxidized LDL levels have been found in AD patients (Maher-Edwards G, De'Ath J, Barnett C, Lavrov A, Lockhart A, Alzheimer's & Dementia: Translational Research & Clinical Interventions. 2015, 1, 131-140; Kassner et al. Current Alzheimer Research, 2008, 5, 358-366; Dildar, et al., Alzheimer Dis Assoc Disord, 24, April-June (2010); Sinem, et al. Current Alzheimer Research, 2010, 7, 463-469). Neuroinflammation and upregulation of multiple inflammatory cytokines were also found in AD patients (Colangelo, et al., Journal of Neuroscience Research, 2002, 70, 462-473; Wyss-Coray, Nature Medicine, 2006, 12 Sep.).

Based on all these findings, Lp-PLA2 is a potential target for the treatment of AD, and this is further confirmed by the clinical results of the Lp-PLA2 inhibitor Rilapladib for AD patients (Maher-Edwards G, De'Ath J, Barnett C, Lavrov A, Lockhart A, *Alzheimer's & Dementia: Translational Research & Clinical Interventions.* 2015, 1, 131-140).

Glaucoma and age-related macular degeneration (AMD) are retinal neurodegenerative diseases. Buschini et al reported that inflammation, including TNF-α signaling, may play an important role in the pathogenesis of glaucoma and AMD (Buschini et al, Progress in Neurobiology, 2011, 95, 14-25; Tezel, Progress in Brain Research, vol. 173, ISSN0079-6123, Chapter 28). Additionally, Shi et al demonstrated that Lp-PLA2 inhibitors can block the release of inflammatory cytokines (Shi, et al, Atherosclerosis, 2007, 191, 54-62). Inhibition of Lp-PLA2 is potential treatment for glaucoma and AMD.

A number of Lp-PLA2 inhibitors have been reported, including β-lactams (Tew D G, Boyd H F, Ashman S, Theobald C, Leach C A. Biochemistry. 1998, 37, 10087-10093), oximes (Jeong T S, Kim M J, Yu H, Kim H S, Choi J K, Kim S S, Lee W S. Bioorg Med Chem Lett. 2005, 15, 1525-1527; Jeong H J, Park Y D, Park H Y, Jeong I Y, Jeong T S, Lee W S. Bioorg Med Chem Lett. 2006, 16, 5576-5579), amides of xanthuric acid (Lin E C, Hu Y, Amantea C M, Pham L M, Cajica J, Okerberg E, Brown H E, Fraser A, Du L, Kohno Y, Ishiyama J, Kozarich J W, Shreder K R. Bioorg Med Chem Lett. 2012, 22, 868-871; Hu Y, Lin E C, Pham L M, Cajica J, Amantea C M, Okerberg E, Brown H E, Fraser A, Du L, Kohno Y, Ishiyama J, Kozarich J W, Shreder K R. Bioorg Med Chem Lett. 2013, 23, 1553-1556), and carbamates (Nagano J M, Hsu K L, Whitby L R, Niphakis M J, Speers A E, Brown S J, Spicer T, Fernandez-Vega V, Ferguson J, Hodder P, Srinivasan P, Gonzalez T D, Rosen H, Bahnson B J, Cravatt B F. Bioorg Med Chem Lett. 2013, 23, 839-843).

The Lp-PLA2 inhibitor Darapladib has been reported as a potential therapy against atherosclerosis and DME (Magrioti V, Kokotos G. *Expert Opin Ther Pat.* 2013; 23: 333-344).

SUMMARY

The present inventors have found that Lp-PLA2 inhibitors play an important role in the treatment of neurodegenerative related diseases, such as Alzheimer's disease (AD), glaucoma and age-related macular degeneration (AMD), or cardiovascular diseases including atherosclerosis. For this reason, the present inventors have developed a novel type of Lp-PLA2 inhibitor, tricyclic pyrimidinone compound.

The tricyclic pyrimidinone compound is a compound having a structure represented by Formula (I) or a pharmaceutically acceptable salt thereof, (I)

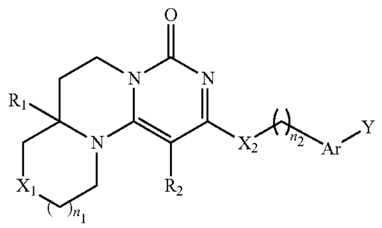

wherein $n_1$ and $n_1$ are each independently 0, 1, or 2;

$R_1$ is selected from —H, cyano, alkyl, deuteroalkyl, deuteroalkoxy, hydroxyalkyl, haloalkyl, haloalkoxy, cycloalkyl, alkoxy;

$R_2$ is selected from —H, cyano, halogen, alkyl, deuteroalkyl, deuteroalkoxy, hydroxyalkyl, haloalkyl, haloalkoxy, cycloalkyl, alkoxy;

$X_1$ and $X_2$ are each independently selected from alkylene, —O—, —S—, or —NR'—, R' is selected from —H, alkyl, deuterated alkyl, or cycloalkyl;

Ar is an arylene or a heteroarylene group, wherein hydrogen atoms in the arylene or heteroarylene are optionally substituted by 1 or more substituents, and the substituents are each independently selected from halogen, alkyl, deuteroalkyl, haloalkyl, alkoxy, deuteroalkoxy, haloalkoxy, hydroxy, hydroxyalkyl, cyano, amino, monoalkyl- or dialkyl-substituted amino, nitro, carboxyl, aldehyde, cycloalkyl, heterocyclyl, aryl, or heteroaryl;

Y is —H, halogen, alkyl, haloalkyl, haloalkoxy, cycloalkyl, alkoxy, deuterated alkyl, deuterated alkoxy, hydroxyl, hydroxyalkyl, cyano, —OAr', —SAr', —NR"—Ar', —NR"R" or —R'"—Ar';

Ar' is selected from aryl or heteroaryl, wherein hydrogen atoms in the aryl or heteroaryl are optionally substituted with one or more substituents, the substituents are each independently selected from halogen, alkyl, haloalkyl, alkoxy, hydroxy, hydroxyalkyl, haloalkoxy, deuterated alkyl, deuterated alkoxy, cyano, amino, nitro, carboxyl, aldehyde, cycloalkyl, heterocyclyl, aryl, or heteroaryl;

R" is H, alkyl or cycloalkyl;

R'" is alkylene;

Optionally, halogens in the "halogen" "haloalkyl" and "haloalkoxy" are each independently selected from F, Cl, Br, or I;

optionally, alkyls in the "alkyl" "deuterated alkyl" "Deuteroalkoxy" "hydroxyalkyl" "haloalkyl" "haloalkoxy", "alkoxy" and "mono- or di-alkyl substituted amino" are each independently $C_1$-$C_{10}$ linear or branched alkyl; optionally each independently $C_1$-$C_7$ linear or branched alkyl; optionally each independently $C_1$-$C_4$ linear or branched alkyl; and optionally selected from methyl, ethyl, n-propyl, isopropyl, n-butyl, isobutyl, tert-butyl, sec-butyl, n-pentyl, 1-methylbutyl, 2-methylbutyl, 3-methylbutyl, isopentyl, 1-ethylpropyl, neopentyl, n-hexyl, 1-methylpentyl, 2-methylpentyl, 3-methylpentyl, isohexyl, 1,1-dimethylbutyl, 2,2-dimethylbutyl, 3,3-dimethylbutyl, 1,2-dimethylbutyl, 1,3-dimethylbutyl, 2,3-dimethylbutyl, 2-ethylbutyl, n-heptyl, 2-methylhexyl, 3-methylhexyl, 2,2-dimethylpentyl, 3,3-dimethylpentyl, 2,3-dimethylpentyl, 2,4-dimethylpentyl, 3-ethylpentyl, or 2,2,3-trimethylbutyl;

optionally, "alkylenes" are each independently $C_1$-$C_{10}$ linear or branched alkylene; optionally each $C_1$-$C_7$ linear or branched alkylene; optionally each $C_1$-$C_5$ linear or branched alkylene; and optionally each selected from methylene, ethylene, n-propylene, isopropylene, n-butylene, iso-butylene, tert-butylene, sec-butylene, n-pentylene, 1-methylbutylene, 2-methylbutylene, 3-methylbutylene, isopentylene, 1-ethylpropylene, neopentylene, n-hexylene, 1-methylpentylene, 2-methylpentylene, 3-methylpentylene, isohexylene, 1,1-dimethylbutylene, 2,2-dimethylbutylene, 3,3-dimethylbutylene, 1,2-dimethylbutylene, 1,3-dimethylbutylene, 2,3-dimethylbutylene, 2-ethylbutylene, n-heptylene, 2-methylhexylene, 3-methylhexylene, 2,2-dimethylpentylene, 3,3-dimethylpentylene, 2,3-dimethylpentylene, 2,4-dimethylpentylene, 3-ethylpentylene, or 2,2,3-trimethylbutylene;

optionally, "cycloalkyl" is $C_3$-$C_{10}$ monocyclic or bicyclic cycloalkyl, optionally $C_3$-$C_7$ monocyclic cycloalkyl, and optionally cyclopropyl, cyclobutyl, cyclopentyl, cyclohexyl, or cycloheptyl;

optionally, "heterocyclyl" is 3- to 10-membered non-aromatic heterocycle ring containing 1, 2, or 3 heteroatoms selected from N, O, and S; optionally 3- to 10-membered non-aromatic ring containing 1 or 2 heteroatoms selected from N and O; optionally 3- to 6-membered non-aromatic ring containing 1 or 2 heteroatoms selected from N and O; optionally 3- to 10-membered non-aromatic ring containing 1 or 2 heteroatoms selected from N and S; and optionally 3- to 6-membered non-aromatic ring containing 1 or 2 heteroatoms selected from N and S;

optionally, "aryl" is 6- to 10-membered aryl; optionally phenyl or naphthyl, and optionally phenyl, 1-naphthyl, or 2-naphthyl;

optionally, "arylene" is 6- to 10-membered arylene; and optionally phenylene or naphthylene;

optionally, "heteroaryl" is 5- to 10-membered heteroaryl ring containing 1-3 heteroatoms selected from N, O, and S; optionally 5- to 10-membered heteroaryl ring containing 1-2 heteroatoms selected from N, O, and S; optionally the heteroaryl ring is selected from pyridine ring, pyrrole ring, pyrazole ring, pyrimidine ring, pyrazine ring, pyridazine ring, thiophene ring, and furan ring; optionally selected from pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl, pyrazin-3-yl, indolyl, isoindolyl, indazolyl, indolizinyl, purinyl, quinolizinyl, quinolinyl, isoquinolinyl, cinnolinyl, phthalazinyl, naphthyridinyl, quinazolinyl, quinoxalinyl, thieno[2,3-b]furanyl, furo[3,2-b]-pyranyl, pyrido[2,3-d]oxazinyl, pyrazolo[4,3-d]oxazolyl, imidazo[4,5-d]thiazolyl, pyrazino[2,3-d]pyridazinyl, imidazo[2,1-b]thiazolyl, imidazo[1,2-b][1,2,4]triazinyl, benzothienyl, benzoxazolyl, benzimidazolyl, benzothiazolyl, benzoxepinyl, benzoxazinyl, benzofuranyl, benzotriazolyl, pyrrolo[2,3-b]pyridyl, pyrrolo[3,2-c]pyridinyl, pyrrolo[3,2-b]pyridyl, imidazo[4,5-b]pyridyl, imidazo[4,5-c]pyridyl, pyrazolo[4,3-d]pyridyl, pyrazolo[4,3-c]pyridyl, pyrazolo[3,4-c]pyridinyl, pyrazolo[3,4-d]pyridyl, pyrazolo[3,4-b]pyridinyl, imidazo[1,2-a]pyridinyl, pyrazolo[ 1,5-a]pyridinyl, pyrrolo[1,2-b]pyridazinyl, imidazo[1,2-c]pyrimidinyl, pyrido[3,2-d]pyrimidinyl, pyrido[4,3-d]pyrimidinyl, pyrido[3,4-d]pyrimidinyl, pyrido[2,3-d]pyrimidinyl, pyrido[2,3-b]pyrazinyl, pyrido[3,4-b]pyrazinyl, pyrimido[5,4-d]pyrimidinyl, pyrazolo[2,3-b]pyrazinyl, or pyrimido[4,5-d]pyrimidinyl; and is optionally selected from pyridin-2-yl, pyridin-3-yl, pyridin-4-yl, pyrimidin-2-yl, pyrimidin-4-yl, or pyrimidin-5-yl;

"heteroarylene" is 5- to 10-membered heteroarylene ring containing 1-3 heteroatoms selected from N, O, and S; optionally 5- to 10-membered heteroaromatic ring containing 1-2 heteroatoms selected from N, O, and S; and optionally the heteroarylene ring is selected from pyridine ring, pyrrole ring, pyrazole ring, pyrimidine ring, pyrazine ring, pyridazine ring, thiophene ring, furan ring optionally, the compound represented by the formula (I) is in the form of tautomers, mesomers, racemates, enantiomers, diastereoisomers, or mixtures of these isomers.

Optionally, $n_1$ and $n_1$ are each independently 0, 1, or 2.

Optionally, $n_1$ is 0 or 1.

Optionally, $n_1$ is 1.

Optionally, $n_1$ is 1.

Optionally, $R_1$ and $R_2$ are each independently selected from —H, $C_1$-$C_2$ hydroxyalkyl (such as —$CH_2OH$, —$CH_2CH_2OH$), cyano, $C_1$-$C_7$ alkyl (such as methyl, ethyl, n-propyl, isopropyl, n-butyl, isobutyl, tert-butyl, sec-butyl, n-pentyl, 1-methylbutyl, 2-methylbutyl, 3-methylbutyl, isopentyl, 1-ethylpropyl, neopentyl, n-hexyl, 1-methylpentyl, 2-methylpentyl, 3-methylpentyl, isohexyl, 1,1-dimethylbutyl, 2,2-dimethylbutyl, 3,3-dimethylbutyl, 1,2-dimethylbutyl, 1,3-dimethylbutyl, 2,3-dimethylbutyl, 2-ethylbutyl, n-heptyl, 2-methylhexyl, 3-methylhexyl, 2,2-dimethylpentyl, 3,3-dimethylpentyl, 2,3-dimethylpentyl, 2,4-dimethylpentyl, 3-ethylpentyl, or 2,2,3-trimethylbutyl), $C_1$-$C_3$ deuteroalkyl (such as —$CD_3$, —$C_2D_5$, or —$C_3D_7$), $C_1$-$C_3$ deuteroalkoxy (such as —$OCD_3$, —$OC_2D_5$, or —$OC_3D_7$), $C_1$-$C_3$ haloalkyl (such as —$CF_3$, —$C_2F_5$, or —$C_3F_7$), $C_1$-$C_7$ haloalkoxy, $C_1$-$C_7$ alkoxy, cyclopropanyl, cyclobutanyl, cyclopentanyl;

optionally, $R_1$ is —H or —$CH_3$ or —$C_2H_5$; optionally, $R_1$ is —H, optionally, $R_2$ is —H;

optionally, $X_1$ and $X_2$ are each independently selected from $C_1$-$C_7$ alkylene, —O—, —S— or —NR'—; optionally, $X_1$ is $C_1$-$C_7$ alkylene (optionally, —$CH_2$—, ethylene, n-propylene, isopropylene, n-butylene, or isobutylene), —O—, —S—, or —NR'—; optionally, $X_1$ is $C_1$-$C_7$ alkylene (optionally, —$CH_2$—, ethylene, n-propylene, isopropylene, n-butylene, or isobutylene), or —O—; optionally, $X_1$ is —$CH_2$— or —O—; optionally, $X_1$ is —O—; optionally, $X_2$ is —O— or —S—; optionally, $X_2$ is —O—;

optionally, R' is selected from —H, $C_1$-$C_7$ alkyl (optionally, methyl, ethyl, n-propyl, isopropyl, n-butyl, isobutyl, tert-butyl, sec-butyl, n-pentyl, 1-methylbutyl, 2-methylbutyl, 3-methylbutyl, isopentyl, 1-ethylpropyl, neopentyl, n-hexyl, 1-methylpentyl, 2-methylpentyl, 3-methylpentyl, isohexyl, 1,1-dimethylbutyl, 2,2-dimethylbutyl, 3,3-dimethylbutyl, 1,2-dimethylbutyl, 1,3-dimethylbutyl, 2,3-dimethylbutyl, 2-ethylbutyl, n-heptyl, 2-methylhexyl, 3-methylhexyl, 2,2-dimethylpentyl, 3,3-dimethylpentyl, 2,3-dimethylpentyl, 2,4-dimethylpentyl, 3-ethylpentyl, or 2,2,3-trimethylbutyl), deuterated alkyl (optionally, —$CD_3$, —$C_2D_5$, or —$C_3D_7$), or $C_3$-$C_6$ cycloalkyl (optionally, cyclopropanyl, cyclobutanyl, cyclopentanyl, or cyclohexanyl);

optionally, Ar is phenylene or pyridyl, wherein hydrogen atoms in the phenylene or pyridyl are optionally substituted with 0, 1, 2, or 3 substituents, the substituents are each independently selected from F, Cl, Br, I, —CN, —Me, —$CF_3$, —$C_2H_5$, —$C_3H_7$, cyclopropyl, cyclobutyl, cyclopentyl, cyclohexyl, —$CD_3$, —$OCD_3$, —OMe, or —$OCF_3$;

optionally, Ar is arylene; optionally Ar is phenylene, wherein the hydrogen atom in the phenylene is optionally substituted by 1 or 2 substituents, and the substituent is halogen; optionally, the substituent is F.

optionally, Y is —H, —F, —Cl, —Br, —I, methyl, ethyl, n-propyl, isopropyl, —$CD_3$, —$OCD_3$, —$CF_3$, —$CHF_2$, —$CH_2F$, —$CH_2CF_3$, —$OCF_3$, —$OCHF_2$, —$OCH_2F$, cyclopropyl, cyclobutyl, cyclopentyl, cyclohexyl, —$OCH_3$, —$OC_2H_5$, —$OC_3H_7$, or —OAr';

optionally, Y is H, halogen, or —OAr'; and optionally, Y is H, —F, or —OAr';

optionally, Ar' is selected from phenyl, pyridyl, pyrimidyl, thienyl, pyrrolyl, pyrazolyl, or quinolinyl, wherein hydrogen atoms in the phenyl, pyridyl, pyrimidyl, thienyl, pyrrolyl, pyrazolyl, or quinolinyl ring are each independently optionally substituted with 1, 2, or 3 substituents, the substituents are each independently selected from F, Cl, Br, —CN, $C_1$-$C_7$ alkyl (optionally, methyl, ethyl, n-propyl, isopropyl, n-butyl, isobutyl, tert-butyl, sec-butyl, n-pentyl, 1-methylbutyl, 2-methylbutyl, 3-methylbutyl, isopentyl, 1-ethylpropyl, neopentyl, n-hexyl, 1-methylpentyl, 2-methylpentyl, 3-methylpentyl, isohexyl, 1,1-dimethylbutyl, 2,2-dimethylbutyl, 3,3-dimethylbutyl, 1,2-dimethylbutyl, 1,3-dimethylbutyl, 2,3-dimethylbutyl, 2-ethylbutyl, n-heptyl, 2-methylhexyl, 3-methylhexyl, 2,2-dimethylpentyl, 3,3-dimethylpentyl, 2,3-dimethylpentyl, 2,4-dimethylpentyl, 3-ethylpentyl, or 2,2,3-trimethylbutyl), —$CD_3$, —$OCD_3$, $C_1$-$C_2$ haloalkyl (such as —$CF_3$, —$CHF_2$, —$CH_2F$, —$CH_2CF_3$), —$OCH_3$, —$OC_2H_7$, —$OC_3H_7$, $C_1$-$C_2$ haloalkoxyl (such as —$OCF_3$, —$OCHF_2$, —$OCH_2F$, —$OCH_2CF_3$), hydroxyl, $C_1$-$C_2$ hydroxyalkyl (such as —$CH_2OH$, —$CH_2CH_2OH$), cyano, $C_3$-$C_6$ cycloalkyl (optionally, cyclopropanyl, cyclobutanyl, cyclopentyl, cyclohexyl); optionally, Ar' is selected from phenyl, pyridyl, or pyrimidinyl; optionally, Ar' is selected from phenyl, pyridin-3-yl, pyridin-4-yl or pyrimidin-5-yl, and is optionally substituted with 1 or 2 substituents, the substituents are selected from F, Cl, Br, $C_1$-$C_4$ alkyl (such as methyl, ethyl, n-propyl, isopropyl, n-butyl base), haloalkyl (such as —$CF_3$, —$CHF_2$, —$CH_2F$) or haloalkoxy (such as —$OCF_3$, —$OCHF_2$, —$OCH_2F$); optionally, the substituent is selected from F, Cl, —$CH_3$, —$CF_3$ or —$OCF_3$;

Optionally, of a compound of Formula (I) or a pharmaceutically acceptable salt thereof, the compound of Formula (I) is selected from the following compounds:

1

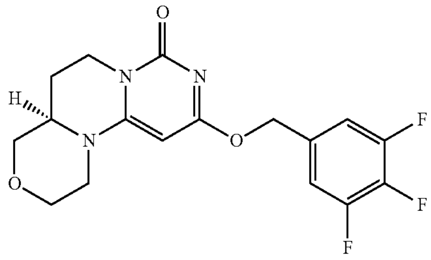

2

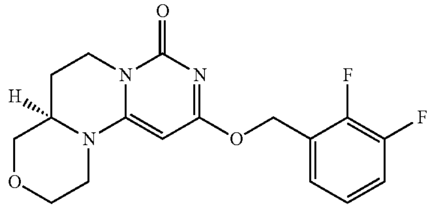

3

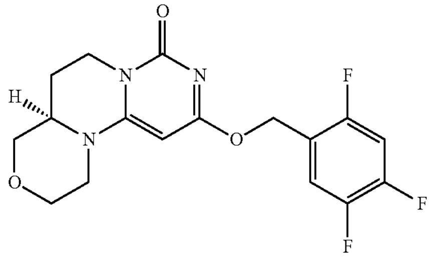

4

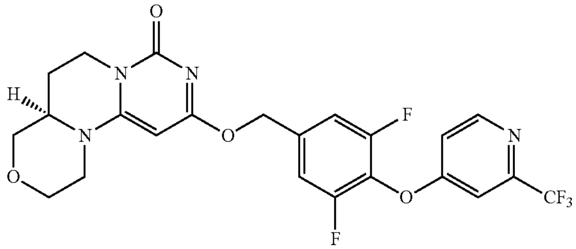

-continued

5

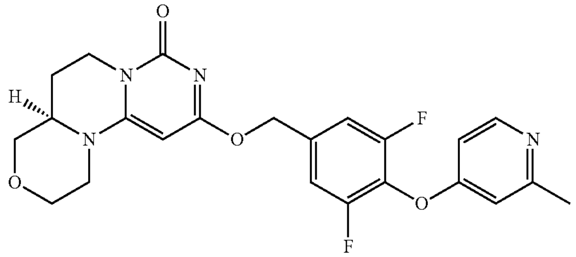

6

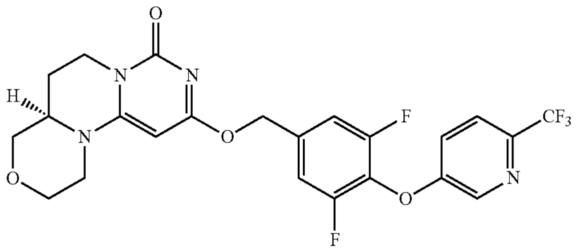

7

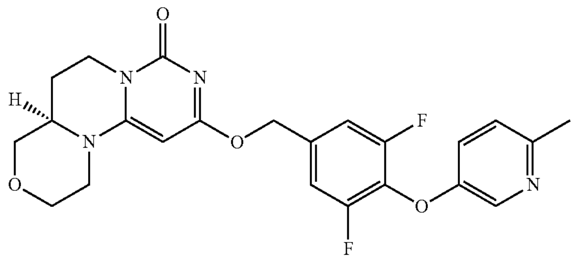

8

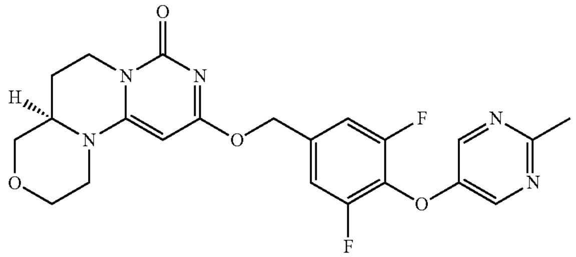

9

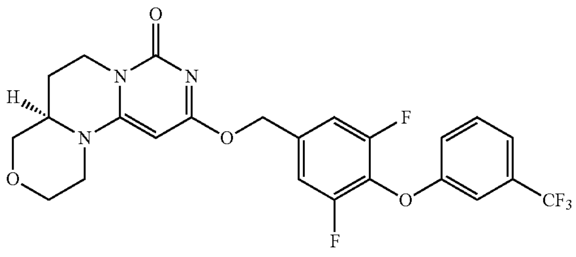

-continued

10

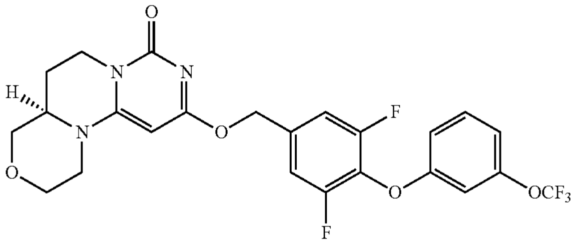

11

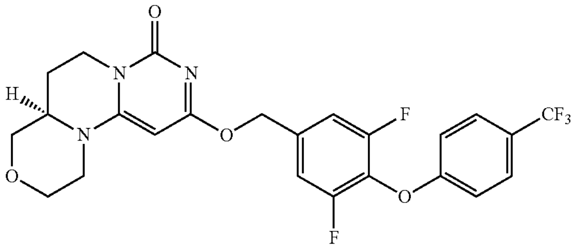

12

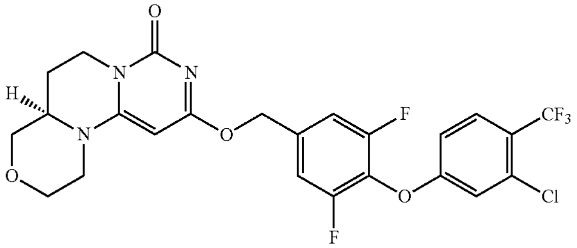

13

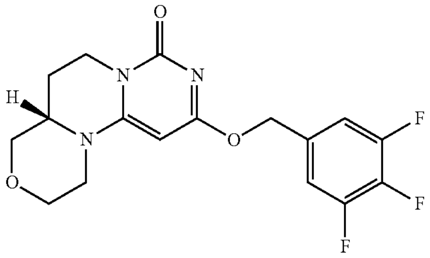

14

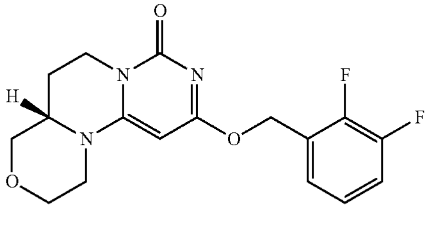

15

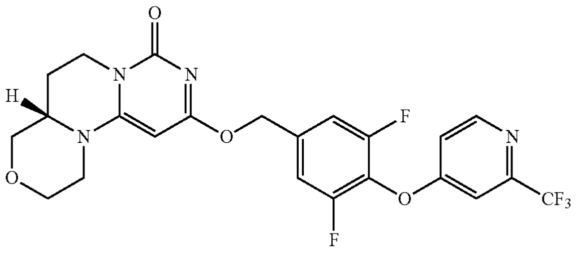

-continued

16

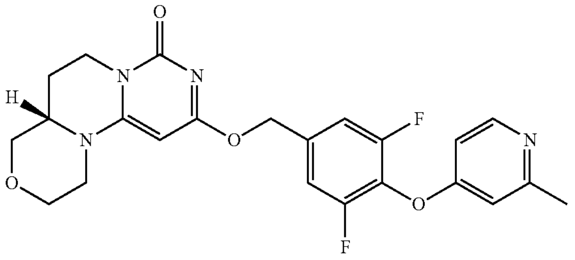

17

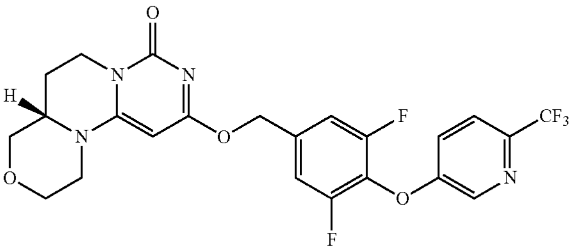

18

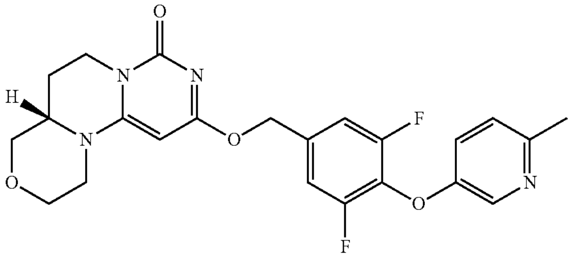

19

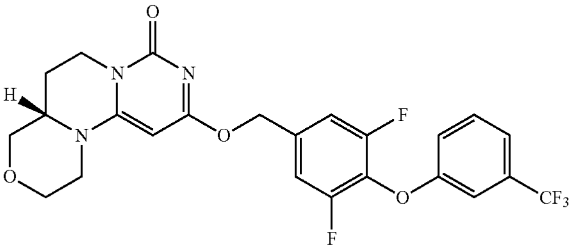

20

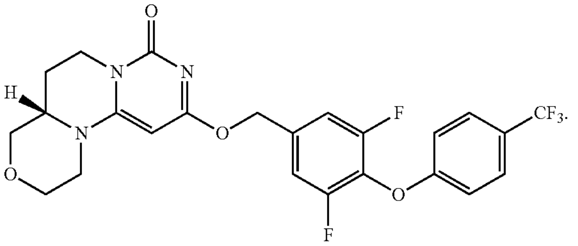

Optionally, the compound of formula (I) or its pharmaceutically acceptable salts, include anionic salts and cationic salts of compounds of formula (I);

optionally, the pharmaceutically acceptable salt includes alkali metal salt, alkaline earth metal salt, or ammonium salt of the compound of Formula (I); optionally, the alkali metal includes sodium, potassium, lithium, or cesium, and the alkaline earth metal includes magnesium, calcium, or strontium;

optionally, the pharmaceutically acceptable salt comprises a compound of formula I with an organic base;

Optionally, the organic base includes trialkylamine, pyridine, quinoline, piperidine, imidazole, picoline, dimethylaminopyridine, dimethylaniline, N-alkylmorpholine, 1,5-diazabicyclo[4.3.0]nonene-5, 1,8-diazabicyclo[5.4.0]undecene-7,1,4-diazabicyclo[2.2.2]octane; optionally, all described trialkylamine comprises trimethylamine, triethylamine, N-ethyldiisopropylamine; optionally, described N-alkylmorpholine comprises N-methylmorpholine;

Optionally, the pharmaceutically acceptable salt comprises a compound of formula I with an acid;

optionally, the acid includes inorganic acid, organic acid; optionally, the inorganic acid includes hydrochloric acid, hydrobromic acid, hydroiodic acid, sulfuric acid, nitric acid, phosphoric acid, carbonic acid; optionally, the organic acid includes formic acid, acetic acid, propionic acid, oxalic acid, malonic acid, succinic acid, fumaric acid, maleic acid, lactic acid, malic acid, citric acid, citric acid, tartaric acid, carbonic acid, picric acid, methanesulfonic acid, ethanesulfonic acid, p-toluenesulfonic acid, glutamic acid, or pamoic acid.

In another aspect, there is provided a preparation method of compound of formula (I) or its pharmaceutically acceptable salt. The preparation method is shown as the below reaction scheme:

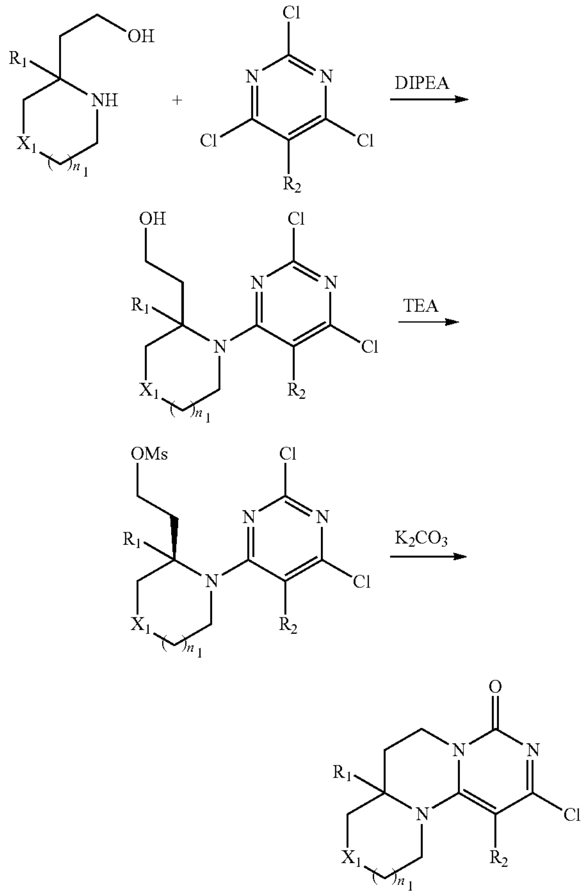

-continued

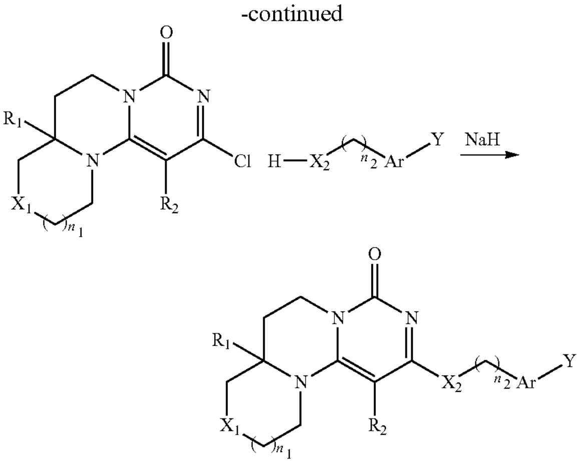

In each of the formulas in the preparation method described above, $n_1$, $n_1$, $R_1$, $R_2$, $X_1$, $X_2$, Ar, and Y are defined as above.

There are no specific limitations for the above reaction conditions. All the reactions can be carried out under conventional conditions.

In another aspect, there is provided a pharmaceutical composition, comprising a therapeutically effective amount of one or more of the compound of Formula (I) or a pharmaceutically acceptable salt thereof, and optionally, a pharmaceutically acceptable excipient(s).

Optionally, the dosage form of the pharmaceutical composition includes oral, rectal, or parenteral formulation;

optionally, the oral formulation includes solid or liquid formulation;

optionally, the solid formulation includes tablet, powder, granule, or capsule;

optionally, the liquid formulation includes aqueous or oily suspension, or syrup;

optionally, the parenteral formulation includes solution for injection, or aqueous or oily suspension.

In another aspect, there is provided the above-mentioned compound of formula (I), or its pharmaceutically acceptable Salt, or the above-mentioned pharmaceutical composition in the preparation of Lp-PLA2 inhibitor.

In another aspect, there is provided the above-mentioned compound of formula (I), or its pharmaceutically acceptable Salt, or the above-mentioned pharmaceutical composition, in the preparation of a medicament for treatment of neurodegeneration-related diseases;

optionally, the neurodegeneration-related diseases include Alzheimer's disease (AD), glaucoma, and age-related macular degeneration (AMD).

In another aspect, there is provided the above-mentioned compound of formula (I), or its pharmaceutically acceptable salt, or the above-mentioned pharmaceutical composition, in the preparation of a medicament for the treatment of cardiovascular diseases, diabetic macular edema (DME), or prostate diseases.

optionally, the cardiovascular diseases include atherosclerosis.

Beneficial effects of the present disclosure are as follows:

The compound of Formula (I) is a tricyclic pyrimidinone compound as an novel Lp-PLA2 inhibitor. It can be used to treat neurodegenerative related diseases such as Alzheimer's disease (AD), glaucoma and age-related macular degeneration (AMD), or cardiovascular diseases including atherosclerosis, diabetic macular edema (DME), or prostate diseases.

DETAILED DESCRIPTION

The present invention is further illustrated by the following examples. It should be understood that the embodiments herein are only used to illustrate the present invention, and do not limit the scope of the present invention in any way.

The starting materials of the present invention can be synthesized by a method known in the art, or be purchased from ABCR GmbH & Co. KG, Acros Organics, Aldrich Chemical Company, Accela ChemBio Inc., and Darry Chemicals, etc.

Unless otherwise specified, the solution in the examples refers to an aqueous solution.

Unless otherwise specified, the temperature in the examples at which the reaction is carried out is room temperature, e.g., 20° C. to 30° C.

Example 1 Preparation of Compound 1

1

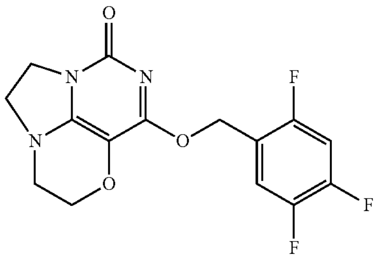

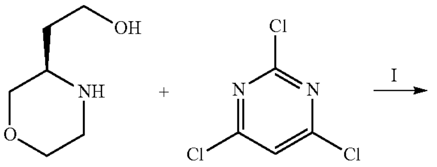

1a 1b

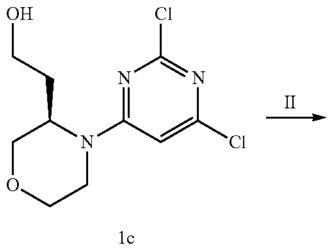

1c

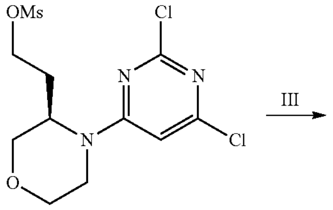

1d

-continued

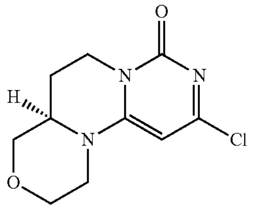

1e

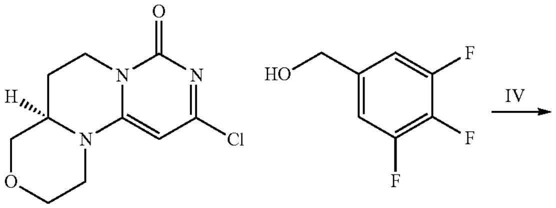

1e 1f

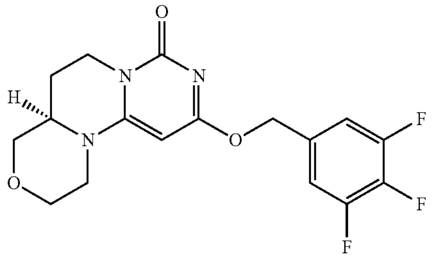

1

Step I: Preparation of Compound 1c

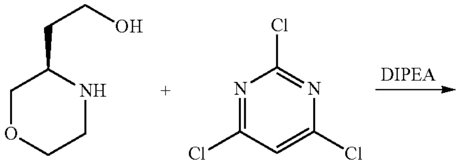

1a 1b

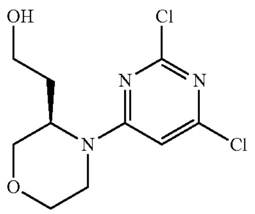

1c

At 0° C., 1a (300 mg, 1.79 mmol), and 1b (360 mg, 1.96 mmol) were dissolved in acetonitrile (2 mL), added DIPEA (0.6 ml, 5.37 mmol), stirred at room temperature for 1 h, concentrated under reduced pressure. Purification via silica gel column chromatography with an eluent system (dichloromethane/methanol=20/1) afforded the title compound 1c (220 mg, Yield: 44.2%) as a white solid.

Steps II and III: Preparation of Compound 1e

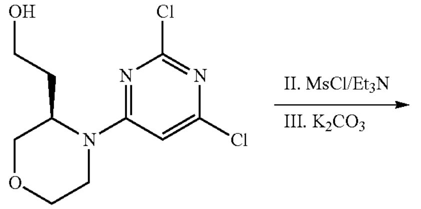

1c

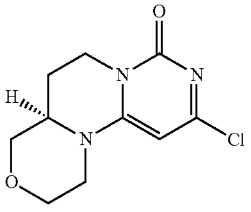

1e

At 0° C., methanesulfonyl chloride (0.07 mL, 0.87 mmol) and 1c (220 mg, 0.79 mmol) were dissolved in dichloromethane (8 mL), then $Et_3N$ (0.33 mL, 2.37 mmol) was added. The reaction was stirred and reacted at room temperature for 1 h, concentrated and proceeded directly to the next reaction. The crude product was dissolved in a mixed solvent of 3/1 dioxane/water (2 mL), followed by addition of potassium carbonate (327 mg, 2.37 mmol) at room temperature. The reaction mixture was stirred at 100° C. for 3 h, concentrated under reduced pressure. Purification via silica gel column chromatography with an eluent system (dichloromethane/methanol=20/1) afforded the title compound 1e (147 mg, Yield: 77%) as a white solid.

$^1$H NMR (400 MHz, $CDCl_3$) δ5.69 (s, 1H), 4.39 (m, 1H), 3.99 (m, 1H), 3.96 (m, 1H), 3.61-3.58 (m, 3H), 3.53 (m, 1H), 3.35-3.25 (m, 2H), 2.18 (m, 1H), 1.72 (m, 1H). MS (ESI): m/z 242.0 $[M+H]^+$○

Step IV: Preparation of Compound 1

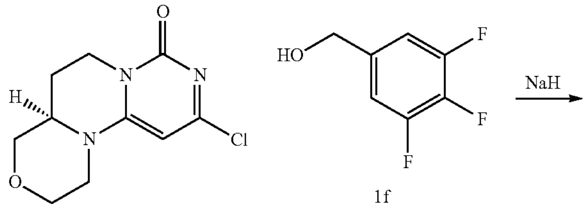

1e 1f

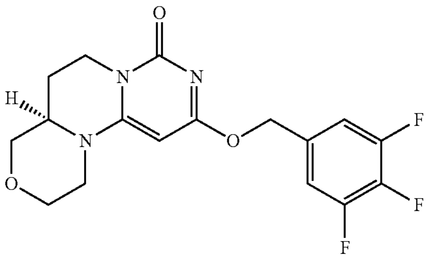

1

To a solution of (3,4,5-Trifluorophenyl)methanol 1f (39 mg, 0.24 mmol) in dry N,N-dimethylformamide (5 mL) was added sodium hydride (60% in mineral oil, 18 mg, 0.44 mmol) at 0° C., and stirred at room temperature for 5 min. Then compound 1e (53 mg, 0.22 mmol) was added, and stirred for 1 h, quenched with a small amount of water. Purification via silica gel column chromatography with an eluent system (dichloromethane/methanol=20/1) afforded the title compound 1 (9.7 mg, 12.0%) as a white solid.

$^1$H NMR (400 MHz, $CDCl_3$) δ 7.30 (m, 2H), 5.42 (s, 2H), 5.21 (s, 1H), 4.33 (m, 1H), 4.01 (m, 1H), 3.94 (m, 1H), 3.72 (m, 1H), 3.62-3.56 (m, 2H), 3.51 (m, 1H), 3.32-3.25 (m, 2H), 2.15 (m, 1H), 1.72 (m, 1H). MS (ESI): m/z 368.1 $[M+H]^+$○

Example 2 Preparation of Compound 2

2

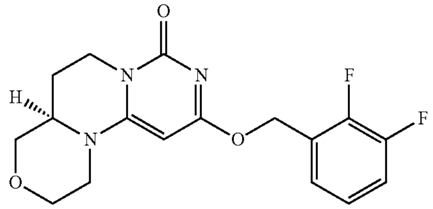

To a solution of (2,3-Difluorophenyl)methanol (35 mg, 0.24 mmol) in dry N,N-dimethylformamide (5 mL) was added sodium hydride (60% in mineral oil, 18 mg, 0.44 mmol) at 0° C., and stirred at room temperature for 5 min. Then compound 1e (53 mg, 0.22 mmol) was added, and stirred for 1 h, quenched with a small amount of water. Purification via silica gel column chromatography with an eluent system (dichloromethane/methanol=20/1) afforded the title compound 2 (11.5 mg, 15%) as a white solid.

$^1$H NMR (400 MHz, $CDCl_3$) δ 7.49 (m, 1H), 6.94-6.80 (m, 2H), 5.42 (s, 2H), 5.22 (s, 1H), 4.34 (m, 1H), 4.01 (m, 1H), 3.93 (m, 1H), 3.71 (m, 1H), 3.63-3.57 (m, 2H), 3.52 (m, 1H), 3.33-3.25 (m, 2H), 2.17 (m, 1H), 1.73 (m, 1H). MS (ESI): m/z 350.1 $[M+H]^+$○

Example 3 Preparation of Compound 3

3

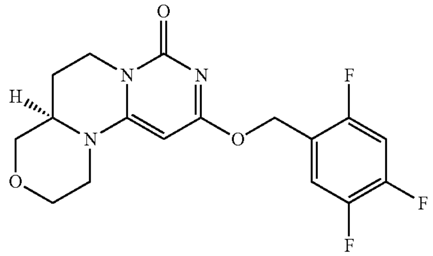

To a solution of (2,4,5-Trifluorophenyl)methanol (39 mg, 0.24 mmol) in dry N,N-dimethylformamide (5 mL) was added sodium hydride (60% in mineral oil, 18 mg, 0.44 mmol) at 0° C., and stirred at room temperature for 5 min. Then compound 1e (53 mg, 0.22 mmol) was added, and stirred for 1 h, quenched with a small amount of water. Purification via silica gel column chromatography with an eluent system (dichloromethane/methanol=20/1) afforded the title compound 3 (14.5 mg, 18%) as a white solid.

$^1$H NMR (400 MHz, $CDCl_3$) δ 7.30 (m, 1H), 6.92 (m, 1H), 5.41 (s, 2H), 5.23 (s, 1H), 4.32 (m, 1H), 4.00 (m, 1H), 3.94 (m, 1H), 3.71 (m, 1H), 3.63-3.56 (m, 2H), 3.52 (m, 1H), 3.34-3.25 (m, 2H), 2.16 (m, 1H), 1.72 (m, 1H). MS (ESI): m/z 368.1 $[M+H]^+$○

Example 4 Preparation of Compound 4

4

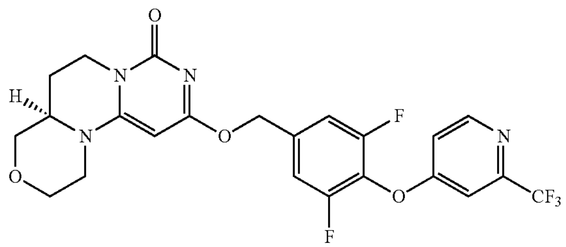

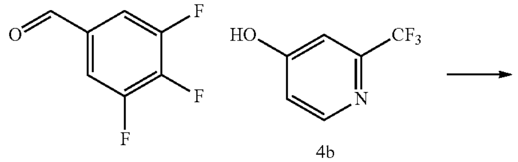

4a 4b

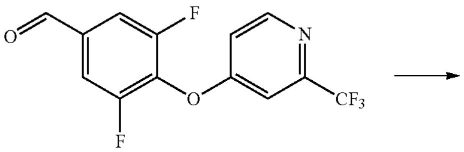

4c

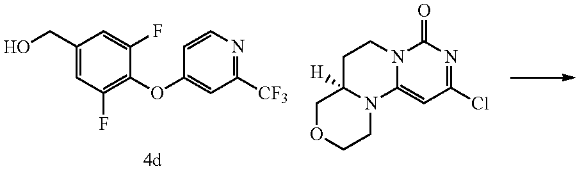

4d 1e

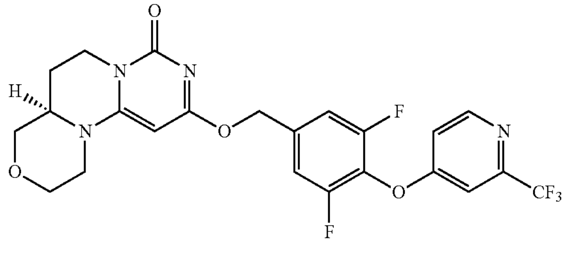

4

Step I: Preparation of Compound 4c 2-(Trifluoromethyl)pyridin-4-ol 4b (0.85 g, 5.2 mmol), 3,4,5-trifluorobenzaldehyde 4a (1 g, 6.2 mmol) and potassium carbonate (0.93 g, 6.76 mmol) were dissolved in N,N-dimethylformamide (DMF) (30 mL) at room temperature. The reaction mixture was stirred at 90° C. for 1 h, cooled to room temperature, followed by addition of ice water (100 mL), extracted with ethyl acetate (50 mL×3). The combined organic phases were washed with saturated aqueous sodium chloride, dried over anhydrous sodium sulfate, filtered to remove the desiccant. The filtrate was concentrated under reduced pressure. Purification via silica gel column chromatography with an eluent system (petroleum ether/ethyl acetate=5/1) afforded the title compound 4c (1.47 g, yield: 93.2%) as a yellow solid.

$^1$H NMR (400 MHz, $CDCl_3$) δ 9.97 (s, 1H), 8.65 (m, 1H), 7.63 (m, 2H), 7.27 (m, 1H), 7.01 (m, 1H)○

Step II: Preparation of Compound 4d

At room temperature, 3,5-difluoro-4-((2-(trifluoromethyl)pyridin-4-yl)oxy)benzaldehyde 4c (1.47 g, 4.85 mmol) was dissolved in ethanol (50 mL), then $NaBH_4$ (184 mg, 4.84 mmol) was added at 0° C. The reaction mixture was stirred at room temperature for 0.5 h, concentrated under reduced pressure, followed by addition of water, extracted with ethyl acetate (100 mL×2). The combined organic phases were washed with saturated sodium chloride solution, dried over anhydrous sodium sulfate, filtered to remove desiccant. The filtrate was concentrated under reduced pressure. Purification via silica gel column chromatography with an eluent system (petroleum ether/ethyl acetate=2/1) afforded the title compound 4d (1.04 g, yield: 70.3%) as a white solid.

$^1$H NMR (400 MHz, $CDCl_3$) δ 8.59 (m, 1H), 7.24 (m, 1H), 7.11 (m, 2H), 6.99 (m, 1H), 4.75 (m, 2H), 2.19 (m, 1H)○

Step III: Preparation of Compound 4

To a solution of (3,5-Difluoro-4-((2-(trifluoromethylpyridin-4-yl)oxy)phenyl)methanol 4d (67 mg, 0.22 mmol) in dry N,N-dimethylformamide (5 mL) was added sodium hydride (60% in mineral oil, 18 mg, 0.44 mmol) at 0° C., and stirred at room temperature for 5 min. Then compound 1e (53 mg, 0.22 mmol) was added, and stirred for 1 h, quenched with a small amount of water. Purification via silica gel column chromatography with an eluent system (dichloromethane/methanol=20/1) afforded the title compound 4 (18 mg, 16%) as a white solid.

$^1$H NMR (400 MHz, $CDCl_3$) δ 8.60 (m, 1H), 7.25 (m, 1H), 7.12 (m, 2H), 6.98 (m, 1H), 5.41 (s, 2H), 5.22 (s, 1H), 4.32 (m, 1H), 4.00 (m, 1H), 3.93 (m, 1H), 3.73 (m, 1H), 3.63-3.56 (m, 2H), 3.51 (m, 1H), 3.31-3.25 (m, 2H), 2.16 (m, 1H), 1.73 (m, 1H). MS (ESI): m/z 511.1 $[M+H]^+$○

Example 5 Preparation of Compound 5

5

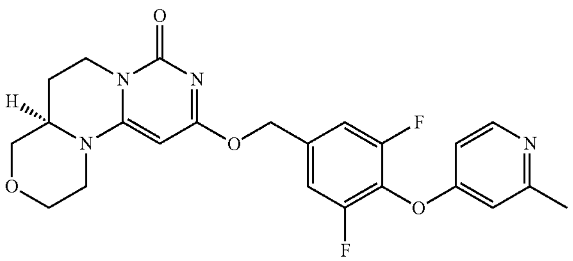

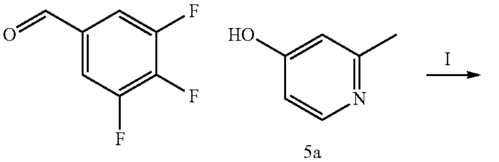

5a 4a

-continued

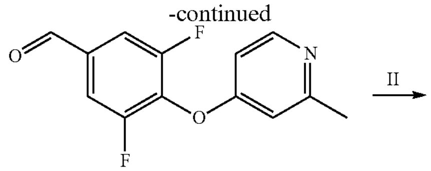

5b

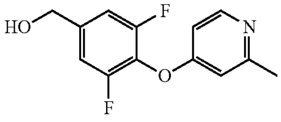

5c

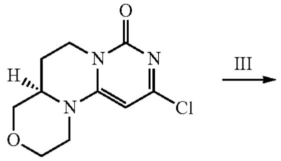

1e

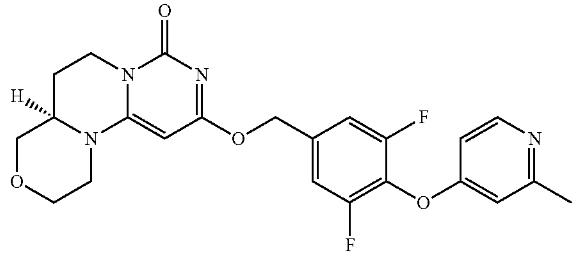

5

Step I: Preparation of Compound 5b

2-Methylpyridin-4-ol 5a (0.5 g, 4.6 mmol), 3,4,5-trifluorobenzaldehyde 4a (0.88 g, 5.5 mmol) and potassium carbonate (0.82 g, 5.95 mmol) were dissolved in N,N-dimethylformamide (DMF) (30 mL) at room temperature. The reaction mixture was stirred at 90° C. for 2 h, cooled to room temperature, followed by addition of ice water (100 mL), extracted with ethyl acetate (50 mL×3). The combined organic phases were washed with saturated aqueous sodium chloride, dried over anhydrous sodium sulfate, filtered to remove the desiccant. The filtrate was concentrated under reduced pressure. Purification via silica gel column chromatography with an eluent system (petroleum ether/ethyl acetate=10/1) afforded the title compound 5b (0.4 g, yield: 34.9%) as a yellow solid.

$^1$H NMR (400 MHz, $CDCl_3$) δ 9.94 (s, 1H), 8.39 (m, 1H), 7.62-7.56 (m, 2H), 6.70-6.66 (m, 2H), 2.52 (s, 3H)○

Step II: Preparation of Compound 5c

At room temperature, 3,5-Difluoro-4-((2-methylpyridin-4-yl)oxy)benzaldehyde 5b (0.4 g, 1.6 mmol) was dissolved in methanol (50 mL), then $NaBH_4$ (71 mg, 1.86 mmol) was added at 0° C. The reaction mixture was stirred at room temperature for 0.5 h, concentrated under reduced pressure, followed by addition of water, extracted with ethyl acetate (100 mL×2). The combined organic phases were washed with saturated sodium chloride solution, dried over anhydrous sodium sulfate, filtered to remove desiccant. The filtrate was concentrated under reduced pressure. Purification via silica gel column chromatography with an eluent system (petroleum ether/ethyl acetate=4/1) afforded the title compound 5c (0.4 g, yield: 99%) as a colorless oil.

$^1$H NMR (400 MHz, $CDCl_3$) δ 8.29 (m, 1H), 7.07 (m, 2H), 6.70-6.64 (m, 2H), 4.73 (s, 2H), 3.20 (m, 1H), 2.50 (s, 3H)○

Step III: Preparation of Compound 5

To a solution of (3,5-Difluoro-4-((2-methyl)pyridin-4-yl)oxy)phenyl)methanol 5c (55 mg, 0.22 mmol) in dry N,N-dimethylformamide (5 mL) was added sodium hydride (60% in mineral oil, 18 mg, 0.44 mmol) at 0° C., and stirred at room temperature for 5 min. Then compound 1e (53 mg, 0.22 mmol) was added, and stirred for 1 h, quenched with a small amount of water. Purification via silica gel column chromatography with an eluent system (dichloromethane/methanol=20/1) afforded the title compound 5 (10 mg, 10%) as a white solid.

$^1$H NMR (400 MHz, $CDCl_3$) δ 8.35 (m, 1H), 7.12 (m, 2H), 6.72-6.65 (m, 2H), 5.42 (s, 2H), 5.22 (s, 1H), 4.33 (m, 1H), 4.02 (m, 1H), 3.94 (m, 1H), 3.73 (m, 1H), 3.65-3.56 (m, 2H), 3.52 (m, 1H), 3.33-3.25 (m, 2H), 2.51 (s, 3H), 2.17 (m, 1H), 1.73 (m, 1H). MS (ESI): m/z 457.1 $[M+H]^+$○

Example 6 Preparation of Compound 6

6

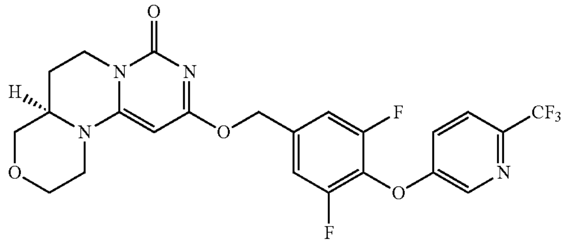

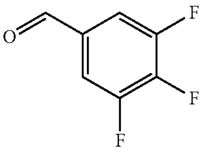

4a

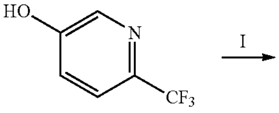

6a

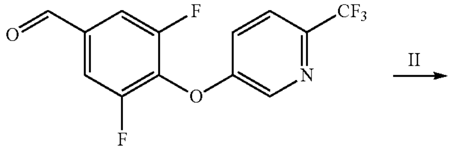

6b

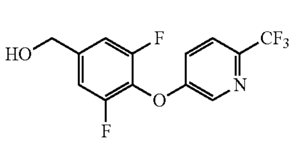

6c

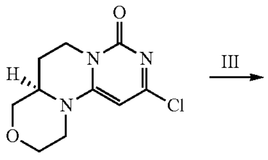

1e

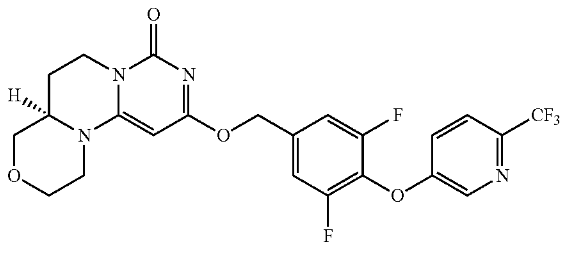

6

Step I: Preparation of Compound 6b 6-(trifluoromethyl)pyridin-3-ol 6a (0.85 g, 5.2 mmol), 3,4,5-trifluorobenzaldehyde 4a (1 g, 6.2 mmol) and potassium carbonate (0.93 g, 6.76 mmol) were dissolved in N,N-dimethylformamide (DMF) (30 mL) at room temperature. The reaction mixture was stirred at 90° C. for 1 h, cooled to room temperature, followed by addition of ice water (100 mL), extracted with ethyl acetate (50 mL×3). The combined organic phases were washed with saturated aqueous sodium chloride, dried over anhydrous sodium sulfate, filtered to remove the desiccant. The filtrate was concentrated under reduced pressure. Purification via silica gel column chromatography with an eluent system (petroleum ether/ethyl acetate=5/1) afforded the title compound 6b (1.34 g, yield: 84.6%) as a yellow solid.

Step II: Preparation of Compound 6c

At room temperature, 3,5-Difluoro-4-((6-(trifluoromethyl)pyridin-3-yl)oxy)benzaldehyde 6b (1.34 g, 4.4 mmol) was dissolved in methanol (50 mL), then $NaBH_4$ (167 mg, 4.4 mmol) was added at 0° C. The reaction mixture was stirred at room temperature for 0.5 h, concentrated under reduced pressure, followed by addition of water, extracted with ethyl acetate (100 mL×2). The combined organic phases were washed with saturated sodium chloride solution, dried over anhydrous sodium sulfate, filtered to remove desiccant. The filtrate was concentrated under reduced pressure. Purification via silica gel column chromatography with an eluent system (petroleum ether/ethyl acetate=2/1) afforded the title compound 6c (0.77 g, yield: 57.4%) as a colorless oil.

$^1H$ NMR (400 MHz, $CDCl_3$) δ 8.46 (s, 1H), 7.63 (m, 1H), 7.30 (m, 1H), 7.09 (m, 2H), 4.73 (m, 2H), 2.40 (m, 1H)○

Step III: Preparation of Compound 6

To a solution of (3,5-Difluoro-4-((6-(trifluoromethyl)pyridin-3-yl)oxy)phenyl)methanol 6c (67 mg, 0.22 mmol) in dry N,N-dimethylformamide (5 mL) was added sodium hydride (60% in mineral oil, 17 mg, 0.42 mmol) at 0° C., and stirred at room temperature for 20 min. Then compound 1e (53 mg, 0.22 mmol) was added, and stirred for 1 h, quenched with a small amount of water. Purification via silica gel column chromatography with an eluent system (dichloromethane/methanol=20/1) afforded the title compound 6 (24.7 mg, 22%) as a white solid.

$^1H$ NMR (400 MHz, $CDCl_3$) δ 8.51 (m, 1H), 7.63 (m, 1H), 7.30 (m, 1H), 7.11 (m, 2H), 5.41 (s, 2H), 5.21 (s, 1H), 4.33 (m, 1H), 4.00 (m, 1H), 3.93 (m, 1H), 3.75 (m, 1H), 3.63-3.56 (m, 2H), 3.52 (m, 1H), 3.31-3.25 (m, 2H), 2.16 (m, 1H), 1.75 (m, 1H). MS (ESI): m/z 511.0 $[M+H]^+$○

Example 7 Preparation of Compound 7

7

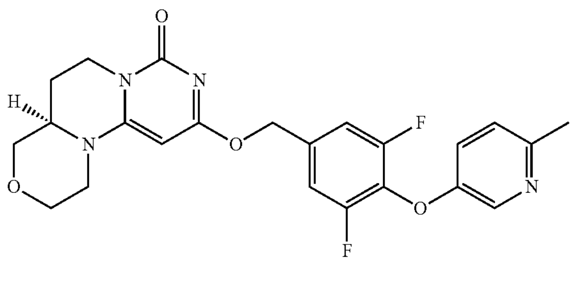

-continued

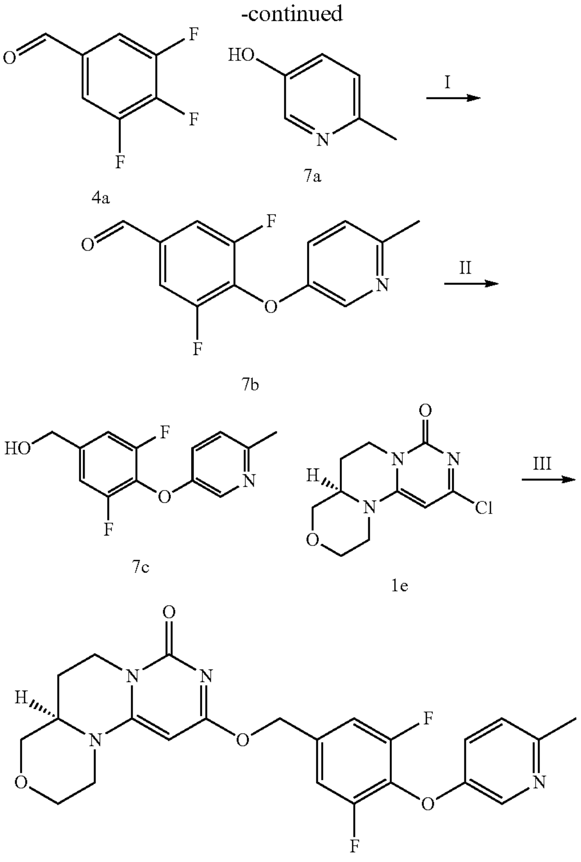

4a 7a 7b 7c 1e 7

Step I: Preparation of Compound 7b

At room temperature, 6-Methylpyridin-3-ol 7a (0.57 g, 5.2 mmol), 3,4,5-trifluorobenzaldehyde 4a (1 g, 6.2 mmol) and potassium carbonate (0.93 g, 6.76 mmol) were dissolved in N,N-dimethylformamide (DMF) (30 mL). The reaction mixture was stirred at 90° C. for 1 h, cooled to room temperature, followed by addition of ice water (100 mL), extracted with ethyl acetate (50 mL×3). The combined organic phases were washed with saturated aqueous sodium chloride, dried over anhydrous sodium sulfate, filtered to remove the desiccant. The filtrate was concentrated under reduced pressure. Purification via silica gel column chromatography with an eluent system (petroleum ether/ethyl acetate=10/1) afforded the title compound 7b (0.91 g, yield: 69.2%) as a yellow solid.

$^1H$ NMR (400 MHz, $CDCl_3$) δ 9.92 (s, 1H), 8.28 (s, 1H), 7.62-7.49 (m, 2H), 7.18-7.10 (m, 2H), 2.54 (s, 3H)○

Step II: Preparation of Compound 7c

At room temperature, 3,5-Difluoro-4-((6-methylpyridin-3-yl)oxy)benzaldehyde 7b (0.91 g, 3.6 mmol) was dissolved in methanol (50 mL), then $NaBH_4$ (161 mg, 4.3 mmol) was added at 0° C. The reaction mixture was stirred at room temperature for 0.5 h, concentrated under reduced pressure, followed by addition of water, extracted with ethyl acetate (100 mL×2). The combined organic phases were washed with saturated sodium chloride solution, dried over anhydrous sodium sulfate, filtered to remove desiccant. The filtrate was concentrated under reduced pressure. Purification via silica gel column chromatography with an eluent system (petroleum ether/ethyl acetate=4/1) afforded the title compound 7c (0.89 g, yield: 98.4%) as a colorless oil.

$^1$H NMR (400 MHz, $CDCl_3$) δ 8.20 (m, 1H), 7.16-6.98 (m, 4H), 4.69 (m, 2H), 2.88 (m, 1H), 2.50 (s, 3H)○

Step III: Preparation of Compound 7

To a solution of (3,5-Difluoro-4-((6-methylpyridin-3-yl)oxy)phenyl)methanol 7c (56 mg, 0.22 mmol) in dry N,N-dimethylformamide (5 mL) was added sodium hydride (60% in mineral oil, 18 mg, 0.44 mmol) at 0° C., and stirred at room temperature for 5 min. Then compound 1e (53 mg, 0.22 mmol) was added, and stirred for 1 h, quenched with a small amount of water. Purification via silica gel column chromatography with an eluent system (dichloromethane/methanol=20/1) afforded the title compound 7 (20 mg, 20%) as a white solid.

$^1$H NMR (400 MHz, $CDCl_3$) δ 8.28 (m, 1H), 7.12 (m, 4H), 5.42 (s, 2H), 5.21 (s, 1H), 4.34 (m, 1H), 4.01 (m, 1H), 3.95 (m, 1H), 3.73 (m, 1H), 3.65-3.56 (m, 2H), 3.51 (m, 1H), 3.35-3.25 (m, 2H), 2.50 (s, 3H), 2.17 (m, 1H), 1.73 (m, 1H). MS (ESI): m/z 457.0 $[M+H]^+$○

Example 8 Preparation of Compound 8

8

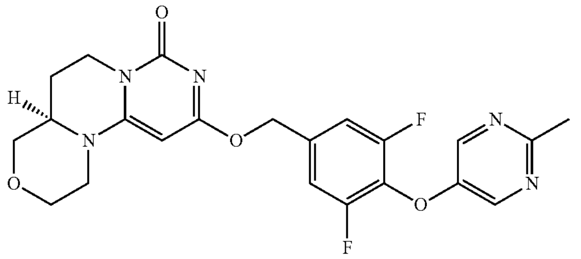

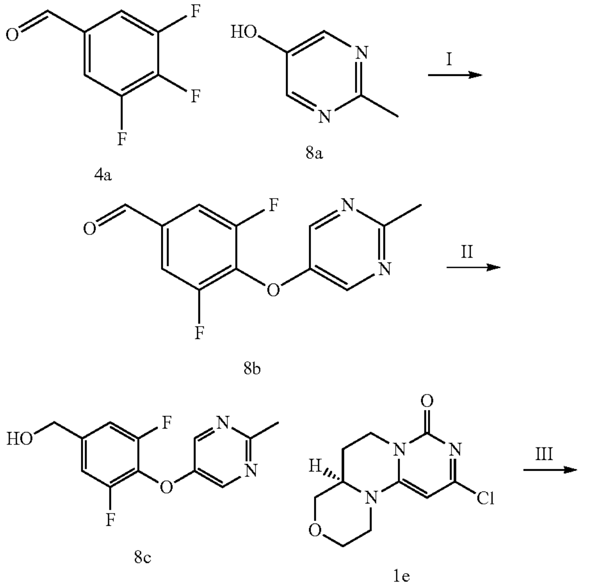

-continued

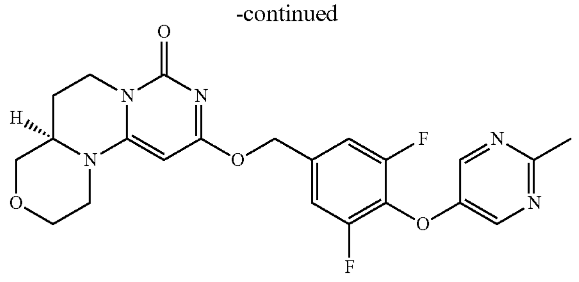

8

Step I: Preparation of Compound 8b

At room temperature, 2-methylpyrimidin-5-ol 8a (0.25 g, 2.3 mmol), 3,4,5-trifluorobenzaldehyde 4a (0.44 g, 2.8 mmol) and potassium carbonate (0.41 g, 2.9 mmol) were dissolved in N,N-dimethylformamide (DMF) (30 mL). The reaction mixture was stirred at 90° C. for 2 h, cooled to room temperature, followed by addition of ice water (100 mL), extracted with ethyl acetate (50 mL×3). The combined organic phases were washed with saturated aqueous sodium chloride, dried over anhydrous sodium sulfate, filtered to remove the desiccant. The filtrate was concentrated under reduced pressure. Purification via silica gel column chromatography with an eluent system (petroleum ether/ethyl acetate=10/1) afforded the title compound 8b (0.24 g, yield: 41.7%) as a yellow solid.

$^1$H NMR (400 MHz, $CDCl_3$) δ 9.93 (s, 1H), 8.39 (s, 2H), 7.64-7.54 (m, 2H), 2.72 (s, 3H)○

Step II: Preparation of Compound 8c

At room temperature, 3,5-Difluoro-4-((2-methylpyrimidin-5-yl)oxy)benzaldehyde 8b (0.24 g, 0.96 mmol) was dissolved in methanol (50 mL), then $NaBH_4$ (30 mg, 0.79 mmol) was added at 0° C. The reaction mixture was stirred at room temperature for 0.5 h, concentrated under reduced pressure, followed by addition of water, extracted with ethyl acetate (100 mL×2). The combined organic phases were washed with saturated sodium chloride solution, dried over anhydrous sodium sulfate, filtered to remove desiccant. The filtrate was concentrated under reduced pressure. Purification via silica gel column chromatography with an eluent system (petroleum ether/ethyl acetate=4/1) afforded the title compound 8c (0.17 g, yield: 70.2%) as a colorless oil.

$^1$H NMR (400 MHz, $CDCl_3$) δ 8.33 (s, 2H), 7.04 (m, 2H), 4.71 (m, 2H), 2.70 (s, 3H)○

Step III: Preparation of Compound 8

To a solution of (3,5-Difluoro-4-((2-methylpyrimidin-5-yl)oxy)phenyl)methanol 8c (56 mg, 0.22 mmol) in dry N,N-dimethylformamide (5 mL) was added sodium hydride (60% in mineral oil, 18 mg, 0.44 mmol) at 0° C., and stirred at room temperature for 5 min. Then compound 1e (53 mg, 0.22 mmol) was added, and stirred for 1 h, quenched with a small amount of water. Purification via silica gel column chromatography with an eluent system (dichloromethane/methanol=20/1) afforded the title compound 8 (13 mg, 13%) as a white solid.

$^1$H NMR (400 MHz, $CDCl_3$) δ 8.34 (s, 2H), 7.10 (m, 2H), 5.44 (s, 2H), 5.23 (s, 1H), 4.34 (m, 1H), 4.02 (m, 1H), 3.93 (m, 1H), 3.73 (m, 1H), 3.64-3.56 (m, 2H), 3.53 (m, 1H), 3.34-3.25 (m, 2H), 2.71 (s, 3H), 2.18 (m, 1H), 1.73 (m, 1H). MS (ESI): m/z 458.0 $[M+H]^+$。

Example 9 Preparation of Compound 9

9

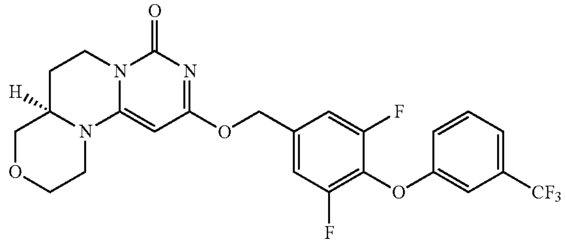

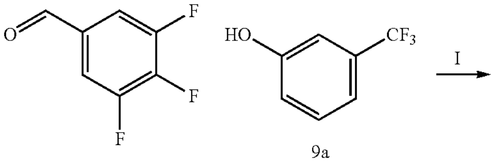

4a

9a

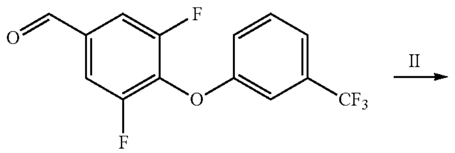

9b

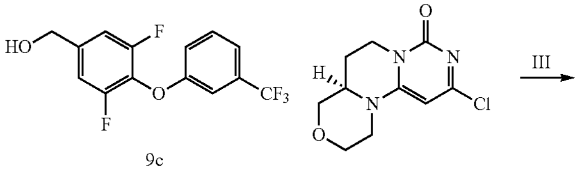

9c

1e

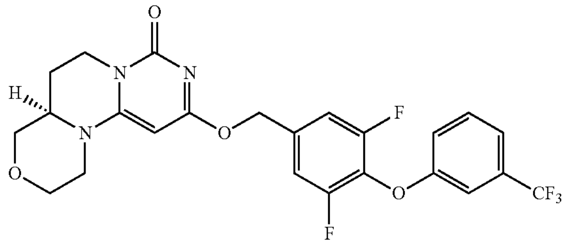

9

Step I: Preparation of Compound 9b

At room temperature, 3-(Trifluoromethyl)phenol 9a (1 g, 6.2 mmol), 3,4,5-trifluorobenzaldehyde 4a (1.09 g, 6.8 mmol) and potassium carbonate (1.1 g, 8.02 mmol) were dissolved in N,N-dimethylformamide (DMF) (30 mL). The reaction mixture was stirred at 90° C. for 2 h, cooled to room temperature, followed by addition of ice water (100 mL), extracted with ethyl acetate (50 mL×3). The combined organic phases were washed with saturated aqueous sodium chloride, dried over anhydrous sodium sulfate, filtered to remove the desiccant. The filtrate was concentrated under reduced pressure. Purification via silica gel column chromatography with an eluent system (petroleum ether/ethyl acetate=10/1) afforded the title compound 9b (1.7 g, yield: 90.7%) as a yellow solid.

$^1$H NMR (400 MHz, $CDCl_3$) δ 9.94 (s, 1H), 7.63-7.55 (m, 2H), 7.46 (m, 1H), 7.39 (m, 1H), 7.21 (s, 1H), 7.13 (m, 1H)。

Step II: Preparation of Compound 9c

At room temperature, 3,5-Difluoro-4-(3-(trifluoromethyl)phenoxy)benzaldehyde 9b (1.7 g, 5.6 mmol) was dissolved in methanol (50 mL), then $NaBH_4$ (213 mg, 5.6 mmol) was added at 0° C. The reaction mixture was stirred at room temperature for 0.5 h, concentrated under reduced pressure, followed by addition of water, extracted with ethyl acetate (100 mL×2). The combined organic phases were washed with saturated sodium chloride solution, dried over anhydrous sodium sulfate, filtered to remove desiccant. The filtrate was concentrated under reduced pressure. Purification via silica gel column chromatography with an eluent system (petroleum ether/ethyl acetate=4/1) afforded the title compound 9c (1.27 g, yield: 74.5%) as a colorless oil.

Step III: Preparation of Compound 9

To a solution of (3,5-Difluoro-4-(3-(trifluoromethyl)phenoxy)phenyl)methanol 9c (73 mg, 0.24 mmol) in dry N,N-dimethylformamide (5 mL) was added sodium hydride (60% in mineral oil, 18 mg, 0.44 mmol) at 0° C., and stirred at room temperature for 5 min. Then compound 1e (53 mg, 0.22 mmol) was added, and stirred for 1 h, quenched with a small amount of water. Purification via silica gel column chromatography with an eluent system (dichloromethane/methanol=20/1) afforded the title compound 9 (8.4 mg, 7.5%) as a white solid.

$^1$H NMR (400 MHz, $CDCl_3$) δ 7.42 (m, 1H), 7.31 (m, 1H), 7.18 (s, 1H), 7.10 (m, 3H), 5.41 (s, 2H), 5.21 (s, 1H), 4.33 (m, 1H), 4.01 (m, 1H), 3.93 (m, 1H), 3.72 (m, 1H), 3.64-3.56 (m, 2H), 3.53 (m, 1H), 3.35-3.25 (m, 2H), 2.16 (m, 1H), 1.72 (m, 1H). MS (ESI): m/z 510.0 $[M+H]^+$。

Example 10 Preparation of Compound 10

10

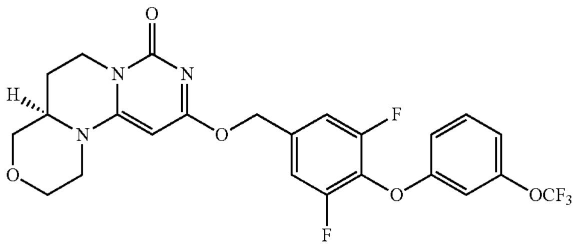

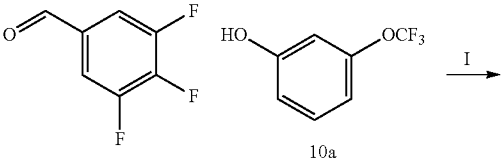

4a

10a

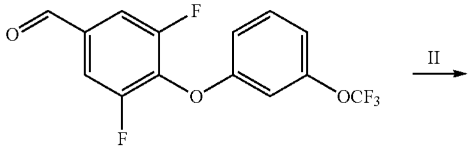

10b

-continued

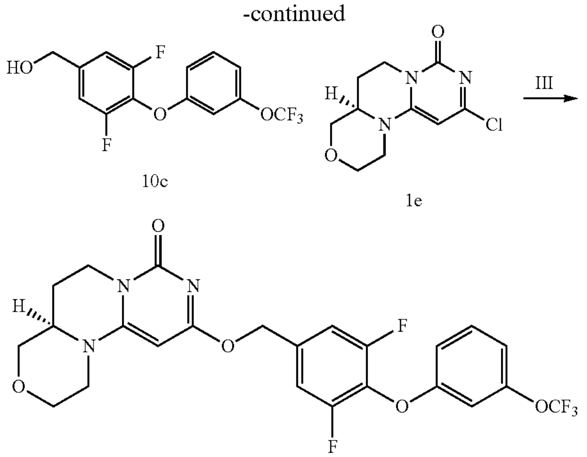

10c

1e

10

Step I: Preparation of Compound 10b

At room temperature, 3-(Trifluoromethoxy)phenol 10a (0.50 g, 2.8 mmol), 3,4,5-trifluorobenzaldehyde 4a (0.5 g, 3.1 mmol) and potassium carbonate (0.5 g, 3.64 mmol) were dissolved in N,N-dimethylformamide (DMF) (30 mL). The reaction mixture was stirred at 90° C. for 2 h, cooled to room temperature, followed by addition of ice water (100 mL), extracted with ethyl acetate (50 mL×3). The combined organic phases were washed with saturated aqueous sodium chloride, dried over anhydrous sodium sulfate, filtered to remove the desiccant. The filtrate was concentrated under reduced pressure. Purification via silica gel column chromatography with an eluent system (petroleum ether/ethyl acetate=10/1) afforded the title compound 10b (0.73 g, yield: 91.8%) as a yellow solid.

$^1$H NMR (400 MHz, $CDCl_3$) δ 9.94 (s, 1H), 7.64-7.54 (m, 2H), 7.34 (m, 1H), 7.00 (m, 1H), 6.87 (m, 2H)○

Step II: Preparation of Compound 10c

At room temperature, 4-(3-(Trifluoromethoxy)phenoxy)-3,5-difluorobenzaldehyde 10b (0.73 g, 2.3 mmol) was dissolved in methanol (50 mL), then $NaBH_4$ (86 mg, 2.28 mmol) was added at 0° C. The reaction mixture was stirred at room temperature for 0.5 h, concentrated under reduced pressure, followed by addition of water, extracted with ethyl acetate (100 mL×2). The combined organic phases were washed with saturated sodium chloride solution, dried over anhydrous sodium sulfate, filtered to remove desiccant. The filtrate was concentrated under reduced pressure. Purification via silica gel column chromatography with an eluent system (petroleum ether/ethyl acetate=4/1) afforded the title compound 10c (0.57 g, yield: 77.4%) as a colorless oil.

$^1$H NMR (400 MHz, $CDCl_3$) δ 7.30 (m, 1H), 7.06 (m, 2H), 6.94 (m, 1H), 6.85 (m, 1H), 6.81 (s, 1H), 4.72 (m, 2H), 1.94 (m, 1H)○

Step III: Preparation of Compound 10

To a solution of 4-(3-(Trifluoromethoxy)phenoxy)-3,5-difluorophenyl)methanol 10c (70 mg, 0.22 mmol) in dry N,N-dimethylformamide (5 mL) was added sodium hydride (60% in mineral oil, 18 mg, 0.44 mmol) at 0° C., and stirred at room temperature for 5 min. Then compound 1e (53 mg, 0.22 mmol) was added, and stirred for 1 h, quenched with a small amount of water. Purification via silica gel column chromatography with an eluent system (dichloromethane/methanol=20/1) afforded the title compound 10 (8.1 mg, 7.0%) as a white solid.

$^1$H NMR (400 MHz, $CDCl_3$) δ 7.28 (m, 1H), 7.08 (m, 2H), 6.91 (m, 1H), 6.88-6.78 (m, 2H), 5.42 (s, 2H), 5.21 (s, 1H), 4.34 (m, 1H), 4.01 (m, 1H), 3.94 (m, 1H), 3.72 (m, 1H), 3.65-3.56 (m, 2H), 3.53 (m, 1H), 3.34-3.25 (m, 2H), 2.18 (m, 1H), 1.74 (m, 1H) MS (ESI): m/z 526.0 $[M+H]^+$○

Example 11 Preparation of Compound 11

11

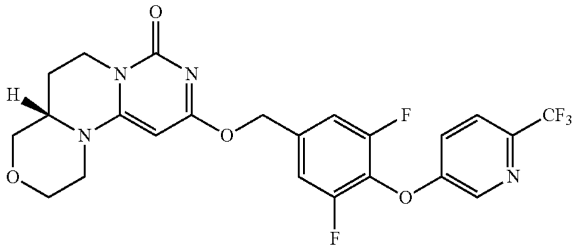

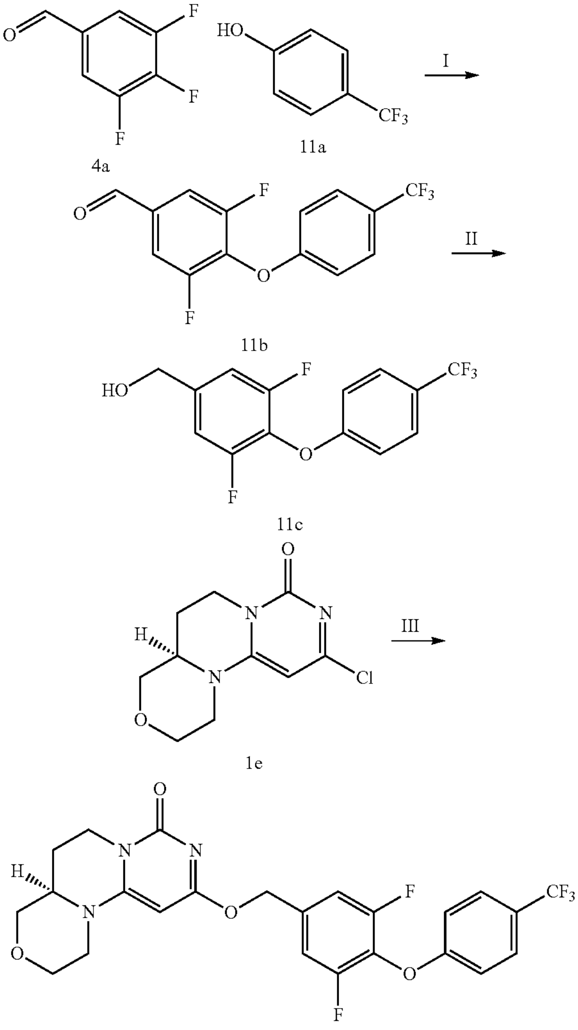

4a

11a

11b

11c

1e

11

Step I: Preparation of compound 11b

At room temperature, 4-(Trifluoromethyl)phenol 11a (0.84 g, 5.2 mmol), 3,4,5-trifluorobenzaldehyde 4a (1 g, 6.2 mmol) and potassium carbonate (0.93 g, 6.76 mmol) were dissolved in N,N-dimethylformamide (DMF) (30 mL). The reaction mixture was stirred at 90° C. for 1 h, cooled to room temperature, followed by addition of ice water (100 mL), extracted with ethyl acetate (50 mL×3). The combined organic phases were washed with saturated aqueous sodium chloride, dried over anhydrous sodium sulfate, filtered to remove the desiccant. The filtrate was concentrated under reduced pressure. Purification via silica gel column chromatography with an eluent system (petroleum ether/ethyl acetate=5/1) afforded the title compound 11b (1.33 g, yield: 84.6%) as a yellow solid.

$^1$H NMR (400 MHz, $CDCl_3$) δ 9.94 (m, 1H), 7.59 (m, 4H), 7.04 (m, 2H)。

Step II: Preparation of Compound 11c

At room temperature, 3,5-Difluoro-4-(4-(trifluoromethyl)phenoxy)benzaldehyde 11b (1.33 g, 4.4 mmol) was dissolved in methanol (50 mL), then $NaBH_4$ (166 mg, 4.4 mmol) was added at 0° C. The reaction mixture was stirred at room temperature for 0.5 h, concentrated under reduced pressure, followed by addition of water, extracted with ethyl acetate (100 mL×2). The combined organic phases were washed with saturated sodium chloride solution, dried over anhydrous sodium sulfate, filtered to remove desiccant. The filtrate was concentrated under reduced pressure. Purification via silica gel column chromatography with an eluent system (petroleum ether/ethyl acetate=2/1) afforded the title compound 11c (0.85 g, yield: 63.5%) as a colorless oil.

$^1$H NMR (400 MHz, $CDCl_3$) δ 7.57 (m, 2H), 7.09-7.00 (m, 4H), 4.72 (m, 2H), 2.03 (m, 1H)。

Step III: Preparation of compound 11

To a solution of 3,5-Difluoro-4-(4-(trifluoromethyl)phenoxy)phenyl)methanol 11c (67 mg, 0.22 mmol) in dry N,N-dimethylformamide (5 mL) was added sodium hydride (60% in mineral oil, 18 mg, 0.44 mmol) at 0° C., and stirred at room temperature for 5 min. Then compound 1e (53 mg, 0.22 mmol) was added, and stirred for 1 h, quenched with a small amount of water. Purification via silica gel column chromatography with an eluent system (dichloromethane/methanol=20/1) afforded the title compound 11 (13.4 mg, 12%) as a white solid.

$^1$H NMR (400 MHz, $CDCl_3$) δ 7.58 (m, 2H), 7.10 (m, 2H), 7.03 (m, 2H), 5.42 (s, 2H), 5.21 (s, 1H), 4.34 (m, 1H), 4.01 (m, 1H), 3.94 (m, 1H), 3.73 (m, 1H), 3.64-3.55 (m, 2H), 3.53 (m, 1H), 3.34-3.25 (m, 2H), 2.17 (m, 1H), 1.72 (m, 1H). MS (ESI): m/z 510.0 $[M+H]^+$。

Example 12 Preparation of Compound 12

12

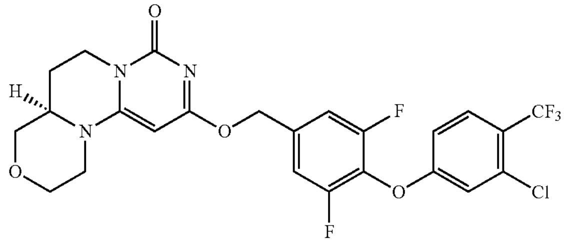

-continued

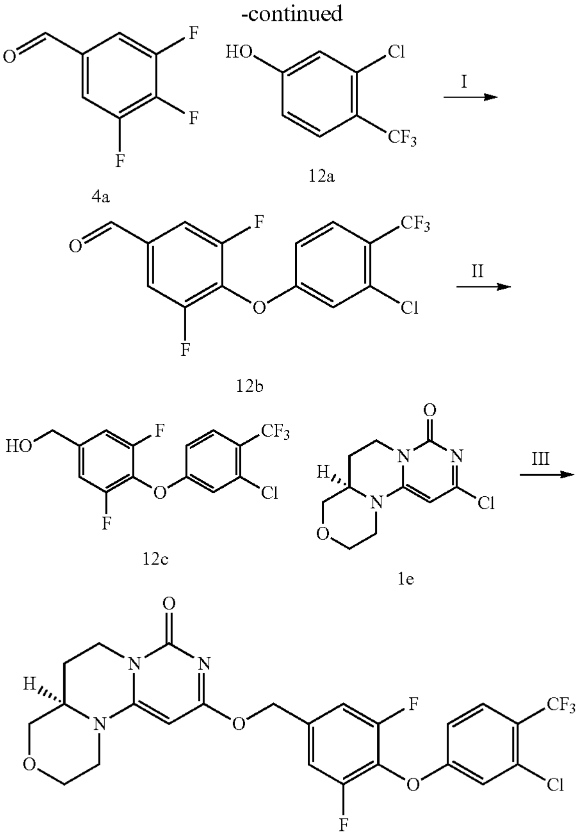

4a

12a

12b

12c

1e

12

Step I: Preparation of Compound 12b

At room temperature, 3-Chloro-4-(trifluoromethyl)phenol 12a (0.25 g, 1.23 mmol), 3,4,5-trifluorobenzaldehyde 4a (0.22 g, 1.4 mmol) and potassium carbonate (0.23 g, 1.65 mmol) were dissolved in N,N-dimethylformamide (DMF) (20 mL). The reaction mixture was stirred at 90° C. for 2 h, cooled to room temperature, followed by addition of ice water (100 mL), extracted with ethyl acetate (50 mL×3). The combined organic phases were washed with saturated aqueous sodium chloride, dried over anhydrous sodium sulfate, filtered to remove the desiccant. The filtrate was concentrated under reduced pressure. Purification via silica gel column chromatography with an eluent system (petroleum ether/ethyl acetate=10/1) afforded the title compound 12b (0.32 g, yield: 77.3%) as a yellow solid.

$^1$H NMR (400 MHz, $CDCl_3$) δ 9.95 (s, 1H), 7.69-7.56 (m, 3H), 7.10 (m, 1H), 6.92 (m, 1H)。

Step II: Preparation of Compound 12c

At room temperature, 4-(3-Chloro-4-(trifluoromethyl)phenoxy)-3,5-difluorobenzaldehyde 12b (0.32 g, 0.95 mmol) was dissolved in methanol (50 mL), then $NaBH_4$ (36 mg, 0.95 mmol) was added at 0° C. The reaction mixture was stirred at room temperature for 0.5 h, concentrated under reduced pressure, followed by addition of water, extracted with ethyl acetate (100 mL×2). The combined organic phases were washed with saturated sodium chloride solution, dried over anhydrous sodium sulfate, filtered to remove desiccant. The filtrate was concentrated under reduced pressure. Purification via silica gel column chromatography with an eluent system (petroleum ether/ethyl acetate=4/1) afforded the title compound 12c (0.15 g, yield: 46.6%) as a white solid.

$^1$H NMR (400 MHz, $CDCl_3$) δ 7.62 (m, 1H), 7.13-7.00 (m, 3H), 6.90 (m, 1H), 4.74 (m, 2H), 1.88 (m, 1H)○

Step III: Preparation of Compound 12

To a solution of (4-(3-Chloro-4-(trifluoromethyl)phenoxy)-3,5-difluorophenyl)methanol 12c (74.5 mg, 0.22 mmol) in dry N,N-dimethylformamide (5 mL) was added sodium hydride (60% in mineral oil, 18 mg, 0.44 mmol) at 0° C., and stirred at room temperature for 5 min. Then compound 1e (53 mg, 0.22 mmol) was added, and stirred for 1 h, quenched with a small amount of water. Purification via silica gel column chromatography with an eluent system (dichloromethane/methanol=20/1) afforded the title compound 12 (17.4 mg, 14.5%) as a white solid.

$^1$H NMR (400 MHz, $CDCl_3$) δ 7.61 (m, 1H), 7.12 (m, 2H), 7.09 (m, 1H), 6.93 (m, 1H), 5.43 (s, 2H), 5.22 (s, 1H), 4.35 (m, 1H), 4.01 (m, 1H), 3.95 (m, 1H), 3.73 (m, 1H), 3.65-3.55 (m, 2H), 3.54 (m, 1H), 3.35-3.25 (m, 2H), 2.17 (m, 1H), 1.73 (m, 1H). MS (ESI): m/z 544.1 $[M+H]^+$○

Example 13 Preparation of Compound 13

13

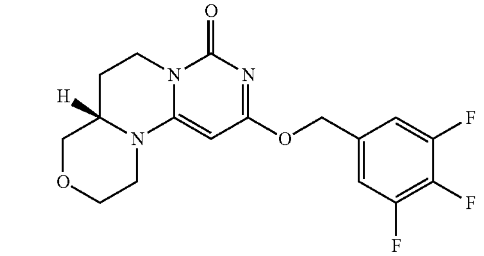

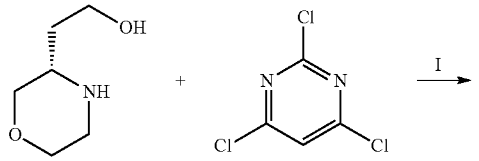

13a 1b

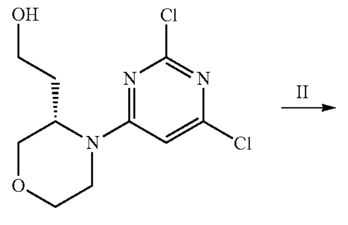

13b

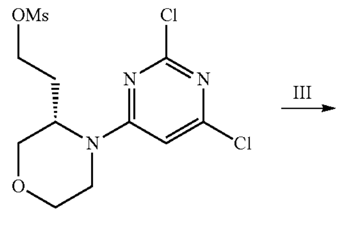

13c

-continued

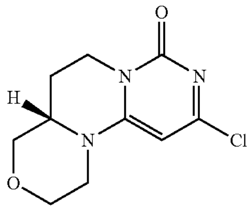

13d

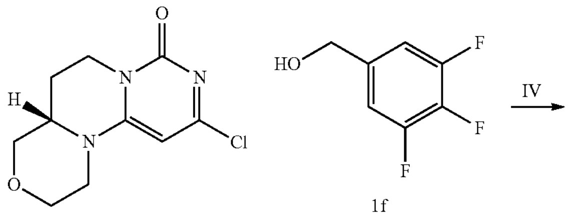

13d 1f

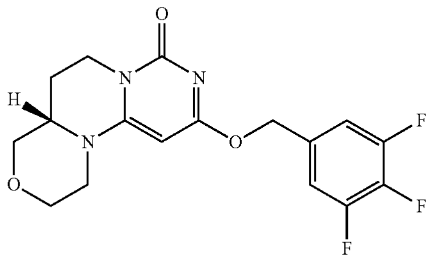

13

Step I: Preparation of Compound 13b

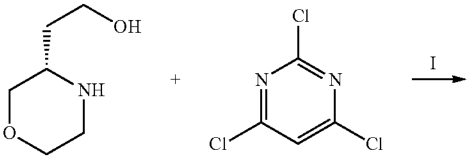

13a 1b

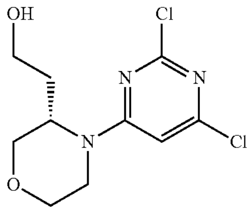

13b

At 0° C., 13a (305 mg, 1.82 mmol), and 1b (370 mg, 2.01 mmol) were dissolved in acetonitrile (2 mL), added DIPEA (0.6 ml, 5.37 mmol), stirred at room temperature for 1 h, concentrated under reduced pressure. Purification via silica gel column chromatography with an eluent system (dichloromethane/methanol=20/1) afforded the title compound 13b (250 mg, Yield: 49.4%) as a white solid.

Step II and III: Preparation of Compound 13d

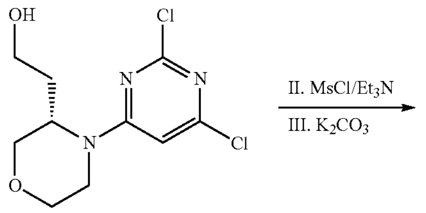

13b

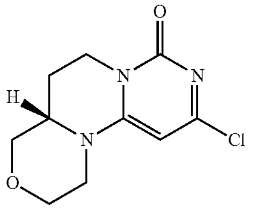

13d

At 0° C., MsCl (0.08 mL, 1.0 mmol) and 13b (250 mg, 0.9 mmol) were dissolved in dichloromethane (8 mL), then $Et_3N$ (0.34 mL, 2.44 mmol) was added. The reaction was stirred and reacted at room temperature for 1 h, concentrated and proceeded directly to the next reaction. The crude product was dissolved in a mixed solvent of 3/1 dioxane/water (2 mL), followed by addition of potassium carbonate (331 mg, 2.4 mmol) at room temperature. The reaction mixture was stirred at 100° C. for 3 h, concentrated under reduced pressure. Purification via silica gel column chromatography with an eluent system (dichloromethane/methanol=20/1) afforded the title compound 13d (160 mg, Yield: 73.6%) as a white solid.

$^1$H NMR (400 MHz, DMSO) δ5.69 (s, 1H), 4.40 (m, 1H), 4.01 (m, 1H), 3.96 (m, 1H), 3.60-3.57 (m, 3H), 3.53 (m, 1H), 3.33-3.25 (m, 2H), 2.18 (m, 1H), 1.73 (m, 1H). MS (ESI): m/z 242.0 [M+H]$^+$ ○

Step IV: Preparation of Compound 13

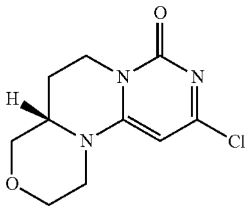

13d

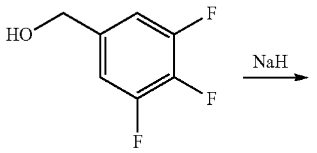

1f

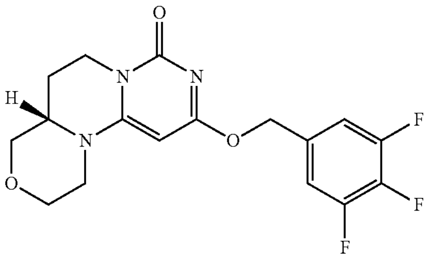

13

To a solution of (3,4,5-Trifluorophenyl)methanol 1f (39 mg, 0.24 mmol) in dry N,N-dimethylformamide (5 mL) was added sodium hydride (60% in mineral oil, 18 mg, 0.44 mmol) at 0° C., and stirred at room temperature for 5 min. Then compound 13d (53 mg, 0.22 mmol) was added, and stirred for 1 h, quenched with a small amount of water. Purification via silica gel column chromatography with an eluent system (dichloromethane/methanol=20/1) afforded the title compound 13 (12 mg, 14.8%) as a white solid.

$^1$H NMR (400 MHz, MeOD) δ 7.32 (m, 2H), 5.42 (s, 2H), 5.21 (s, 1H), 4.34 (m, 1H), 4.01 (m, 1H), 3.93 (m, 1H), 3.73 (m, 1H), 3.63-3.56 (m, 2H), 3.51 (m, 1H), 3.32-3.25 (m, 2H), 2.16 (m, 1H), 1.73 (m, 1H). MS (ESI): m/z 368.1 [M+H]$^+$ ○

Example 14 Preparation of Compound 14

14

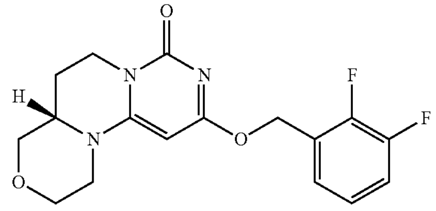

To a solution of (2,3-Difluorophenyl)methanol (35 mg, 0.24 mmol) in dry N,N-dimethylformamide (5 mL) was added sodium hydride (60% in mineral oil, 18 mg, 0.44 mmol) at 0° C., and stirred at room temperature for 5 min. Then compound 13d (53 mg, 0.22 mmol) was added, and stirred for 1 h, quenched with a small amount of water. Purification via silica gel column chromatography with an eluent system (dichloromethane/methanol=20/1) afforded the title compound 14 (15 mg, 19.6%) as a white solid.

$^1$H NMR (400 MHz, $CDCl_3$) δ7.49 (m, 1H), 6.94-6.80 (m, 2H), 5.41 (s, 2H), 5.22 (s, 1H), 4.35 (m, 1H), 4.01 (m, 1H), 3.93 (m, 1H), 3.72 (m, 1H), 3.63-3.57 (m, 2H), 3.53 (m, 1H), 3.35-3.25 (m, 2H), 2.17 (m, 1H), 1.73 (m, 1H). MS (ESI): m/z 350.1 [M+H]$^+$ ○

Example 15 Preparation of Compound 15

15

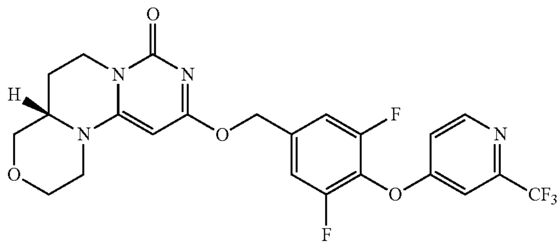

To a solution of (3,5-Difluoro-4-((2-(trifluoromethylpyridin-4-yl)oxy)phenyl)methanol 4d (67 mg, 0.22 mmol) in dry N,N-dimethylformamide (5 mL) was added sodium hydride (60% in mineral oil, 18 mg, 0.44 mmol) at 0° C., and stirred at room temperature for 5 min. Then compound 13d (53 mg, 0.22 mmol) was added, and stirred for 1 h, quenched with a small amount of water. Purification via silica gel column chromatography with an eluent system (dichloromethane/methanol=20/1) afforded the title compound 15 (23 mg, 20.4%) as a white solid.

$^1$H NMR (400 MHz, $CDCl_3$) δ 8.60 (m, 1H), 7.23 (s, 1H), 7.12 (m, 2H), 7.03 (m, 1H), 5.41 (s, 2H), 5.22 (s, 1H), 4.33 (m, 1H), 4.02 (m, 1H), 3.93 (m, 1H), 3.73 (m, 1H), 3.65-3.56 (m, 2H), 3.53 (m, 1H), 3.32-3.25 (m, 2H), 2.18 (m, 1H), 1.73 (m, 1H). MS (ESI): m/z 511.1 $[M+H]^+$○

Example 16 Preparation of Compound 16

16

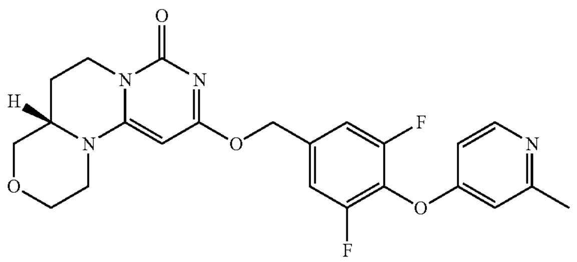

To a solution of (3,5-Difluoro-4-((2-methyl)pyridin-4-yl)oxy)phenyl)methanol 5c (55 mg, 0.22 mmol) in dry N,N-dimethylformamide (5 mL) was added sodium hydride (60% in mineral oil, 18 mg, 0.44 mmol) at 0° C., and stirred at room temperature for 5 min. Then compound 13d (53 mg, 0.22 mmol) was added, and stirred for 1 h, quenched with a small amount of water. Purification via silica gel column chromatography with an eluent system (dichloromethane/methanol=20/1) afforded the title compound 16 (15 mg, 15%) as a white solid.

$^1$H NMR (400 MHz, $CDCl_3$) δ 8.35 (m, 1H), 7.11 (m, 2H), 6.71-6.63 (m, 2H), 5.42 (s, 2H), 5.21 (s, 1H), 4.35 (m, 1H), 4.02 (m, 1H), 3.93 (m, 1H), 3.73 (m, 1H), 3.63-3.56 (m, 2H), 3.53 (m, 1H), 3.34-3.25 (m, 2H), 2.51 (s, 3H), 2.18 (m, 1H), 1.73 (m, 1H). MS (ESI): m/z 457.1 $[M+H]^+$○

Example 17 Preparation of Compound 17

17

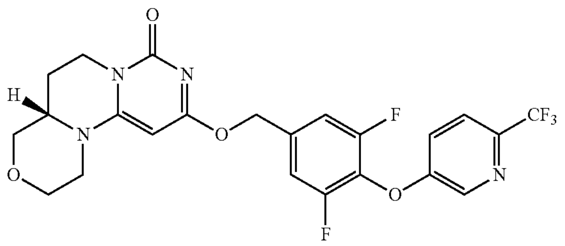

To a solution of (3,5-Difluoro-4-((6-(trifluoromethyl)pyridin-3-yl)oxy)phenyl)methanol 6c (67 mg, 0.22 mmol) in dry N,N-dimethylformamide (5 mL) was added sodium hydride (60% in mineral oil, 17 mg, 0.42 mmol) at 0° C., and stirred at room temperature for 20 min. Then compound 13d (53 mg, 0.22 mmol) was added, and stirred for 1 h, quenched with a small amount of water. Purification via silica gel column chromatography with an eluent system (dichloromethane/methanol=20/1) afforded the title compound 17 (20.0 mg, 17.8%) as a white solid.

$^1$H NMR (400 MHz, $CDCl_3$) δ 8.51 (m, 1H), 7.63 (m, 1H), 7.30 (m, 1H), 7.11 (m, 2H), 5.41 (s, 2H), 5.22 (s, 1H), 4.35 (m, 1H), 4.00 (m, 1H), 3.93 (m, 1H), 3.74 (m, 1H), 3.65-3.56 (m, 2H), 3.53 (m, 1H), 3.32-3.25 (m, 2H), 2.17 (m, 1H), 1.76 (m, 1H). MS (ESI): m/z 511.1 $[M+H]^+$○

Example 18 Preparation of Compound 18

18

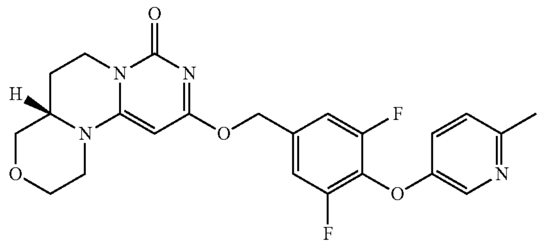

To a solution of (3,5-Difluoro-4-((6-methylpyridin-3-yl)oxy)phenyl)methanol 7c (56 mg, 0.22 mmol) in dry N,N-dimethylformamide (5 mL) was added sodium hydride (60% in mineral oil, 18 mg, 0.44 mmol) at 0° C., and stirred at room temperature for 5 min. Then compound 13d (53 mg, 0.22 mmol) was added, and stirred for 1 h, quenched with a small amount of water. Purification via silica gel column chromatography with an eluent system (dichloromethane/methanol=20/1) afforded the title compound 18 (16 mg, 16%) as a white solid.

$^1$H NMR (400 MHz, $CDCl_3$) δ 8.28 (m, 1H), 7.12 (m, 4H), 5.42 (s, 2H), 5.22 (s, 1H), 4.33 (m, 1H), 4.01 (m, 1H), 3.93 (m, 1H), 3.73 (m, 1H), 3.63-3.56 (m, 2H), 3.53 (m, 1H), 3.34-3.25 (m, 2H), 2.50 (s, 3H), 2.18 (m, 1H), 1.75 (m, 1H). MS (ESI): m/z 457.1 $[M+H]^+$○

Example 19 Preparation of Compound 19

19

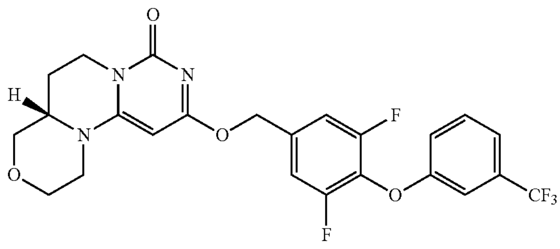

To a solution of (3,5-Difluoro-4-(3-(trifluoromethyl)phenoxy)phenyl)methanol 9c (73 mg, 0.24 mmol) in dry N,N-dimethylformamide (5 mL) was added sodium hydride (60% in mineral oil, 18 mg, 0.44 mmol) at 0° C., and stirred at room temperature for 5 min. Then compound 13d (53 mg, 0.22 mmol) was added, and stirred for 1 h, quenched with a small amount of water. Purification via silica gel column chromatography with an eluent system (dichloromethane/methanol=20/1) afforded the title compound 19 (12.3 mg, 11%) as a white solid.

$^1H$ NMR (400 MHz, $CDCl_3$) δ 7.43 (m, 1H), 7.30 (m, 1H), 7.17 (s, 1H), 7.12 (m, 3H), 5.42 (s, 2H), 5.21 (s, 1H), 4.35 (m, 1H), 4.01 (m, 1H), 3.93 (m, 1H), 3.73 (m, 1H), 3.65-3.56 (m, 2H), 3.53 (m, 1H), 3.34-3.25 (m, 2H), 2.17 (m, 1H), 1.73 (m, 1H). MS (ESI): m/z 510.1 $[M+H]^+$○

Example 20 Preparation of Compound 20

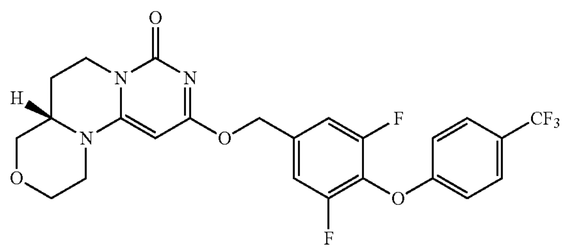

To a solution of 3,5-Difluoro-4-(4-(trifluoromethyl)phenoxy)phenyl)methanol 11c (67 mg, 0.22 mmol) in dry N,N-dimethylformamide (5 mL) was added sodium hydride (60% in mineral oil, 18 mg, 0.44 mmol) at 0° C., and stirred at room temperature for 5 min. Then compound 13d (53 mg, 0.22 mmol) was added, and stirred for 1 h, quenched with a small amount of water. Purification via silica gel column chromatography with an eluent system (dichloromethane/methanol=20/1) afforded the title compound 20 (16.8 mg, 15%) as a white solid.

$^1H$ NMR (400 MHz, $CDCl_3$) δ 7.58 (m, 2H), 7.12 (m, 2H), 7.01 (m, 2H), 5.42 (s, 2H), 5.22 (s, 1H), 4.35 (m, 1H), 4.01 (m, 1H), 3.93 (m, 1H), 3.73 (m, 1H), 3.63-3.55 (m, 2H), 3.53 (m, 1H), 3.35-3.25 (m, 2H), 2.16 (m, 1H), 1.73 (m, 1H). MS (ESI): m/z 510.1 $[M+H]^{30}$ ○

Biological Evaluation

The biological activity of the compounds can be determined by using any suitable assay and tissue and in vivo models for determining the activity of the compounds as LpPLA2 inhibitors.

(1) Recombinant Human Lp-PLA2 (rhLp-PLA2) Assay (also Known as PED6 Assay)

PED6 is a fluorescently labeled phospholipid that can be purchased directly from Invitogene or Molecular Probes. There is a fluorescence-quenching p-nitrophenyl group on the Sn3 position, and a Bodipy fluorescein (FL) group on the sn2 position. Once it is cleaved by the Lp-PLA2 enzyme, the FL group is released, resulting in enhanced fluorescence. However, Lp-PLA2 inhibitors can prevent this cleavage, so that no fluorescence enhancement is observed Assay method: The compound to be tested (as shown in Table 1) was mixed with DMSO solution at a volume ratio of 1:3, diluted to prepare a source plate of a 384-well microplate. Then 0.01 µl of the compound was transferred via an ECHO liquid dispenser from the source plate to a 384-well Greiner 784076 plate, and 5 microliters of a buffer composed of 50 mM HEPES, pH 7.4, 150 mM NaCl, 1 mM CHAPS (the buffer solution contains Recombinant human Lp-PLA2 enzyme at a concentration of 4 nM or 110 pM) was added to each well on the plate. The plate was centrifuged at 500 rpm for 10 seconds. After 30 minutes of pre-incubation, 5 microliters of the above buffer solution was added to a 384-well Greiner784076 plate, and the plate was centrifuged at 500 rpm for 10 seconds. After the plate was incubated at room temperature for 20 min in the dark, the fluorescence intensity was read at ex 480/em 540 with a ViewLux microplate imager, and the Excel's XL fitting model was used to perform curve and QC analysis to calculate pIC50. The results are listed in Table 1.

TABLE 1

| Compound No. | rhLp-PLA2 ($pIC_{50}$) |
|---|---|
| 1 | 8.4 |
| 2 | 7.6 |
| 3 | 7.5 |
| 4 | 10.1 |
| 5 | 10.2 |
| 6 | 10.0 |
| 7 | 10.2 |
| 8 | 9.5 |
| 9 | 10.2 |
| 10 | 10.1 |
| 11 | 10.1 |
| 12 | 10.3 |
| 13 | 8.2 |
| 14 | 7.5 |
| 15 | 9.9 |
| 16 | 10.1 |
| 17 | 9.9 |
| 18 | 10.0 |
| 19 | 10.1 |
| 20 | 10.0 |
| Positive Compound Rilapladib | 8.9 |

(2) Human Plasma Lp-PLA2 Assay (Also Known as Thio-PAF Assay)

The human plasma assay was conducted using the sulphatide analog of PAF (phosphatidylcholine), which is hydrolyzed to produce phospholipids containing free sulfhydryl groups, subjected to Michael addition with CPM to generate fluorescence-enhancing maleimide.

Continuous quantitative analysis of thiol could be conducted by detecting the fluorescence intensity.

This assay can be used to detect the inhibitory activity of the Lp-PLA2 inhibitor on the Lp-PLA2 enzyme in human plasma.

Assay Method: The compound to be tested (as shown in Table 2) was mixed with a DMSO solution in a volume ratio of (1:3), and diluted to prepare a source plate of a 384-well microplate. Then 0.01 µl of the compound was transferred via an ECHO liquid dispenser from the source plate to a 384-well Greiner 784076 low-volume plate, and 8 µl of pre-aliquoted and frozen mixed human plasma was added. The plate was centrifuged at 500 rpm for 10 seconds. After a 30 min pre-incubation, 2 µl of a substrate solution, and containing 2.5 mM 2-thio-PAF (a solution in ethanol), 32 µM CPM (a solution in DMSO) and a buffer of 3.2 mM N-ethylmaleimide (NEM) (a buffer solution consisting of 50 mM HEPES, pH 7.4, 150 mM NaCl, 1 mM CHAPS) was added by a BRAVO liquid handling station to a 384-well Greiner 784076 low-volume plate. After 2 min, the reaction was quenched with 5 µl of 5% trifluoroacetic acid. After the plate was incubated at room temperature for 40 min in a dark place, the fluorescence intensity was read at ex 380/em 485 with an Envision microplate reader, and the XL fitting model in Excel was used to perform the curve analysis and QC analysis to calculate pIC50. The results are shown in Table 2.

TABLE 2

| Compound No. | Thio-PAF ($pIC_{50}$) |
|---|---|
| 1 | 7.2 |
| 2 | 6.6 |
| 3 | 6.5 |
| 4 | 8.2 |
| 5 | 8.5 |
| 6 | 8.1 |
| 7 | 8.1 |
| 8 | 7.8 |
| 9 | 8.2 |
| 10 | 8.0 |
| 11 | 8.1 |
| 12 | 8.2 |
| 13 | 7.1 |
| 14 | 6.5 |
| 15 | 7.9 |
| 16 | 8.1 |
| 17 | 7.9 |
| 18 | 8.0 |
| 19 | 8.1 |
| 20 | 7.9 |
| Positive compound Rilapladib | 7.8 |

What is claimed is:

1. A compound of Formula (I) or a pharmaceutically acceptable salt thereof, (I)

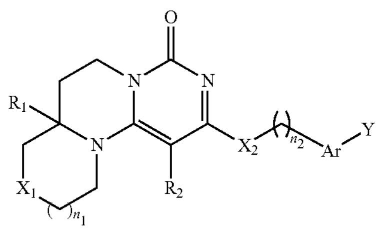

wherein $n_1$, and $n_2$ are each independently 0, 1, or 2;

$R_1$ is selected from H, cyano, alkyl, deuterated alkyl, deuterated alkoxy, hydroxyalkyl, haloalkyl, haloalkoxy, cycloalkyl, alkoxy;

$R_2$ is selected from H, cyano, halogen, alkyl, deuterated alkyl, deuterated alkoxy, hydroxyalkyl, haloalkyl, haloalkoxy, cycloalkyl, alkoxy;

$X_1$ and $X_2$ are each independently selected from alkylene, —O—, —S—, or —NR'—, R' is selected from H, alkyl, deuterated alkyl, or cycloalkyl;

Ar is an arylene group or a heteroarylene group, wherein hydrogen atoms in the arylene or heteroarylene are optionally substituted by 1 or more substituents, and the substituents are each independently selected from halogen, alkyl, deuteroalkyl, haloalkyl, alkoxy, deuteroalkoxy, haloalkoxy, hydroxy, hydroxyalkyl, cyano, amino, monoalkyl- or dialkyl-substituted amino, nitro, carboxyl, —C(O)—H, cycloalkyl, aryl, or heteroaryl;

Y is H, halogen, alkyl, haloalkyl, haloalkoxy, cycloalkyl, alkoxy, deuterated alkyl, deuterated alkoxy, hydroxy, hydroxyalkyl, cyano, —OAr', —SAr', —NR"—Ar', —NR"R", or —R'"—Ar';

Ar' is selected from aryl or heteroaryl, wherein hydrogen atoms in the aryl or heteroaryl are optionally substituted with one or more substituents, the substituents are each independently selected from halogen, alkyl, deuterated alkyl, haloalkyl, alkoxy, hydroxy, hydroxyalkyl, haloalkoxy, deuteroalkyl, deuterated alkoxy, cyano, amino, nitro, carboxyl, —C(O)—H, cycloalkyl, aryl, or heteroaryl;

R" is H, alkyl, or cycloalkyl;

R'" is alkylene;

wherein, halogens in the "halogen" "haloalkyl" and "haloalkoxy" are each independently selected from F, Cl, Br, or I;

the alkyl in the "alkyl" "deuterated alkyl" "deuterated alkoxy" "hydroxyalkyl" "haloalkyl" "haloalkoxy", "alkoxy" and "mono- or di-alkyl substituted amino" are each independently $C_1$-$C_{10}$ linear or branched alkyl;

"alkylenes" are each independently $C_1$-$C_{10}$ linear or branched alkylene;

"cycloalkyl" is $C_3$-$C_{10}$ monocyclic or bicyclic cycloalkyl;

"aryl" is 6- to 10-membered aryl;

"arylene" is 6- to 10-membered arylene;

"heteroaryl" is 5- to 10-membered heteroaryl ring containing 1-3 heteroatoms selected from N, O, and S;

"heteroarylene" is 5- to 10-membered heteroarylene ring containing 1-3 heteroatoms selected from N, O, and S.

2. The compound or a salt thereof according to claim 1, wherein, alkyls in the "alkyl" "deuterated alkyl" "deuterated alkoxy" "hydroxyalkyl" "haloalkyl" "haloalkoxy", "alkoxy" and "mono- or di-alkyl substituted amino" are each independently $C_1$-$C_7$ linear or branched alkyl; "alkylenes" are each independently $C_1$-$C_7$ linear or branched alkylene; "cycloalkyl" is $C_3$-$C_7$ monocyclic cycloalkyl;

"aryl" is phenyl or naphthyl;

"arylene" is phenylene or naphthylene;

"heteroaryl" is 5- to 10-membered heteroaryl ring containing 1-2 heteroatoms selected from N, O, and S;

"heteroarylene" is 5- to 10-membered heteroaromatic ring containing 1-2 heteroatoms selected from N, O, and S.

3. The compound or a salt thereof according to claim 1, wherein $n_1$ is 0 or 1; $n_2$ is 1, $R_1$ and $R_2$ are each independently selected from H, —$CH_2OH$, —$CH_2CH_2OH$, cyano, methyl, ethyl, n-propyl, isopropyl, n-butyl, isobutyl, tert-butyl, sec-butyl, n-pentyl, 1-methylbutyl, 2-methylbutyl, 3-methylbutyl, isopentyl, 1-ethylpropyl, neopentyl, n-hexyl, 1-methylpentyl, 2-methylpentyl, 3-methylpentyl, isohexyl, 1,1-dimethylbutyl, 2,2-dimethylbutyl, 3,3-dimethylbutyl, 1,2-dimethylbutyl, 1,3-dimethylbutyl, 2,3-dimethylbutyl, 2-ethylbutyl, n-heptyl, 2-methylhexyl, 3-methylhexyl, 2,2-dimethylpentyl, 3,3-dimethylpentyl, 2,3-dimethylpentyl, 2,4-dimethylpentyl, 3-ethylpentyl, or 2,2,3-trimethylbutyl, —$CD_3$, —$C_2D_5$, or —$C_3D_7$, —$OCD_3$, —$OC_2D_5$, or —$OC_3D_7$, —$CF_3$, —$C_2F_5$, or —$C_3F_7$, $C_1$-$C_7$ haloalkoxy, $C_1$-$C_7$ alkoxy, cyclopropanyl, cyclobutanyl, cyclopentanyl;

$X_1$ is —$CH_2$—, ethylene, n-propylene, isopropylene, n-butylene, or isobutylene, —O—, —S—; $X_2$ is —O— or —S—;

Ar is phenylene or pyridyl, wherein hydrogen atoms in the phenylene or pyridyl are optionally substituted with 1, 2, or 3 substituents, the substituents are each independently selected from F, Cl, Br, I, —CN, —Me, —$CF_3$, —$C_2H_5$, —$C_3H_7$, cyclopropyl, cyclobutyl, cyclopentyl, cyclohexyl, —$CD_3$, —$OCD_3$, —OMe, or —$OCF_3$;

Y is H, —F, —Cl, —Br, —I, methyl, ethyl, n-propyl, isopropyl, —$CD_3$, —$OCD_3$, —$CF_3$, —$CHF_2$, —$CH_2F$, —$CH_2CF_3$, —$OCF_3$, —$OCHF_2$, —$OCH_2F$, cyclopropyl, cyclobutyl, cyclopentyl, cyclohexyl, $-OCH_3$, $-OC_2H_5$, $-OC_3H_7$, or —OAr';

Ar' is selected from phenyl, pyridyl, pyrimidyl, thienyl, pyrrolyl, pyrazolyl, or quinolinyl, wherein hydrogen atoms in the phenyl, pyridyl, pyrimidyl, thienyl, pyrrolyl, pyrazolyl, or quinolinyl ring are each independently optionally substituted with 1, 2, or 3 substituents, the substituents are each independently selected from F, Cl, Br, methyl, ethyl, n-propyl, isopropyl, n-butyl, isobutyl, tert-butyl, sec-butyl, n-pentyl, 1-methylbutyl, 2-methylbutyl, 3-methylbutyl, isopentyl, 1-ethylpropyl, neopentyl, n-hexyl, 1-methylpentyl, 2-methylpentyl, 3-methylpentyl, isohexyl, 1,1-dimethylbutyl, 2,2-dimethylbutyl, 3,3-dimethylbutyl, 1,2-dimethylbutyl, 1,3-dimethylbutyl, 2,3-dimethylbutyl, 2-ethylbutyl, n-heptyl, 2-methylhexyl, 3-methylhexyl, 2,2-dimethylpentyl, 3,3-dimethylpentyl, 2,3-dimethylpentyl, 2,4-dimethylpentyl, 3-ethylpentyl, or 2,2,3-trimethylbutyl, $-CD_3$, $-OCD_3$, $-CF_3$, $-CHF_2$, $-CH_2F$, $-CH_2CF_3$, $-OCH_3$, $-OC_2H_7$, $-OC_3H_7$, $-OCF_3$, $-OCHF_2$, $-OCH_2F$, $-OCH_2CF_3$, hydroxyl, $-CH_2OH$, $-OCH_2CH_2OH$, —CN, or cyclopropanyl, cyclobutanyl, cyclopentanyl, or cyclohexanyl.

4. The compound of Formula (I) or a pharmaceutically acceptable salt thereof according to claim 1, wherein the compound of Formula (I) is selected from the following compounds:

1

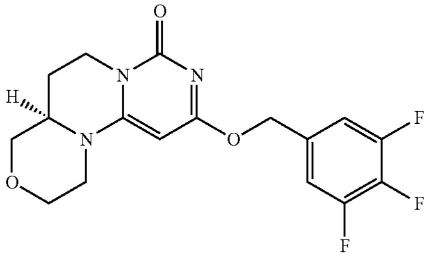

2

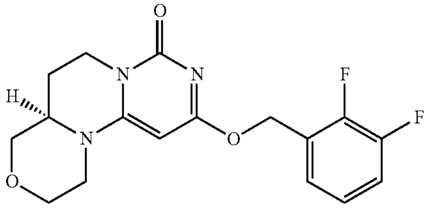

3

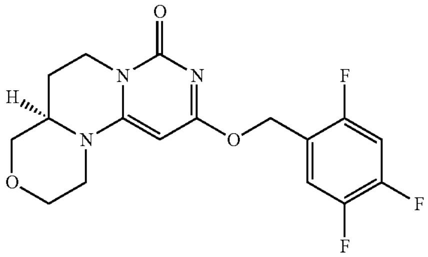

-continued

4

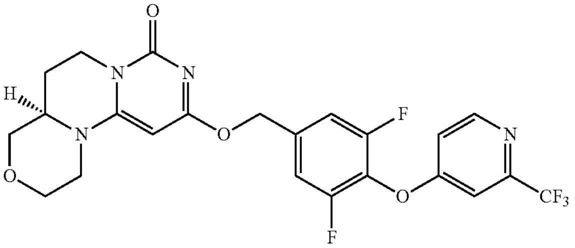

5

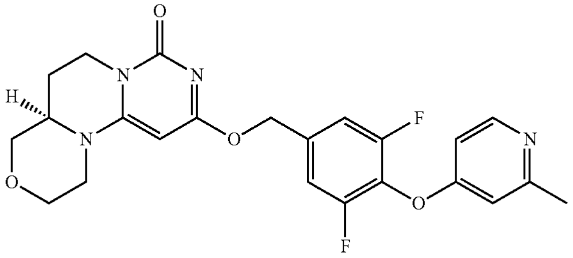

6

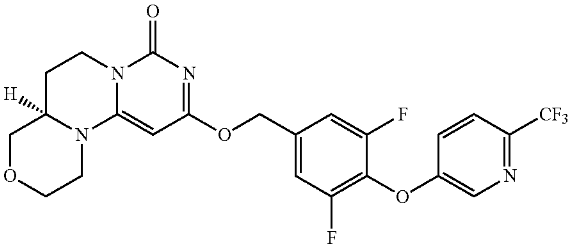

7

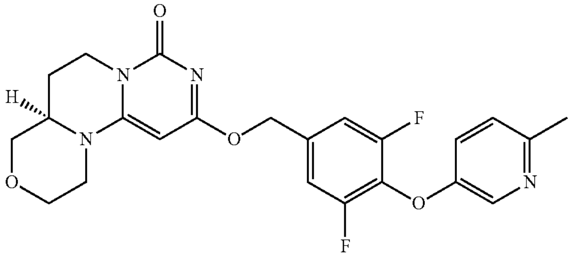

8

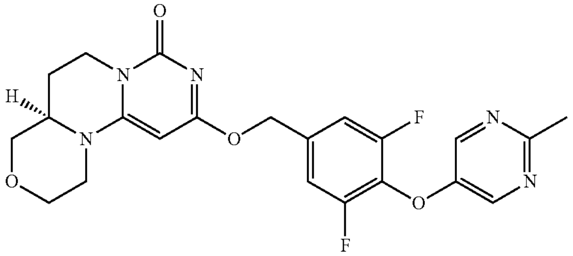

-continued
9
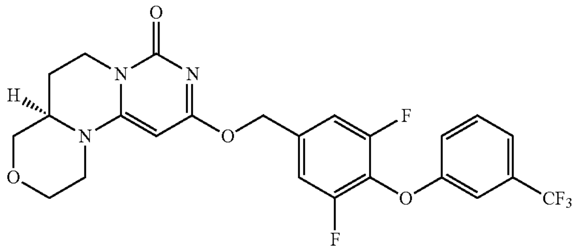
10
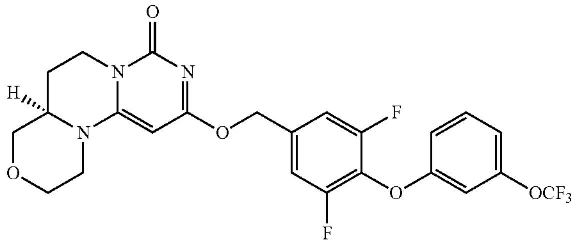
11
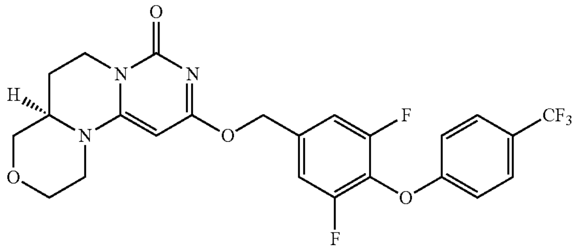
12
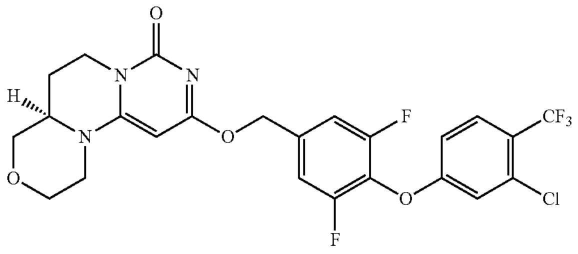
13
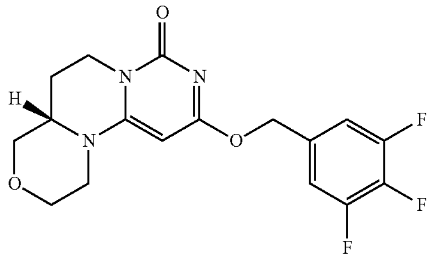
14
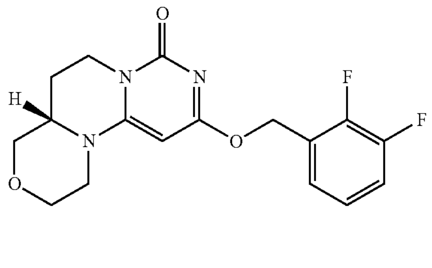
-continued
15
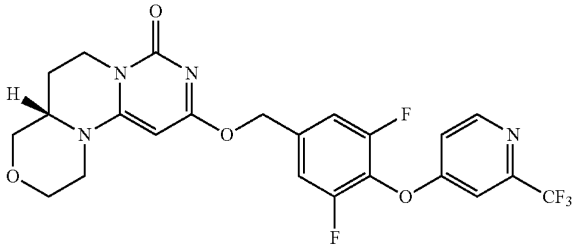
16
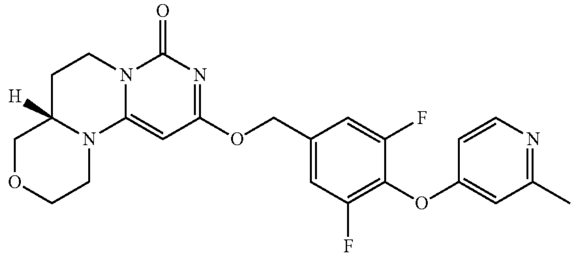
17
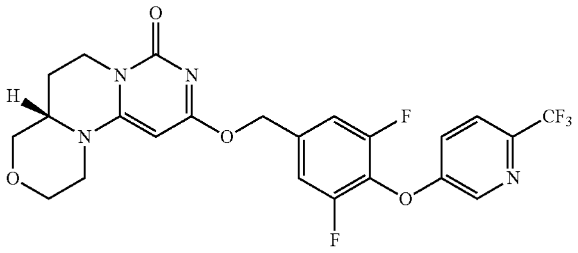
18
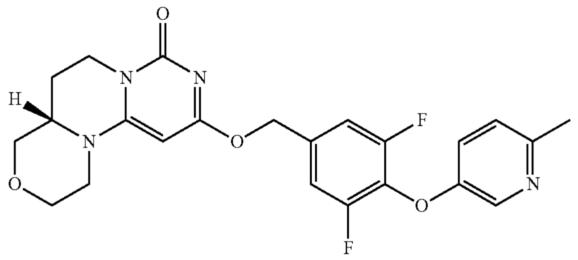
19
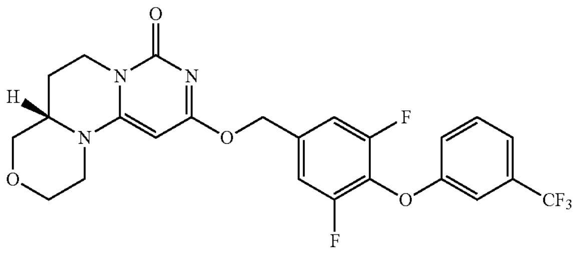

-continued

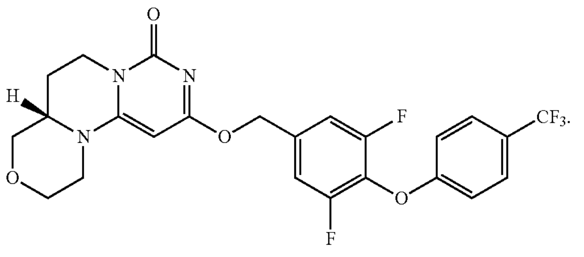

5. The compound of Formula (I) or a pharmaceutically acceptable salt thereof according to claim 1, wherein the pharmaceutically acceptable salt is selected from a group consisting of an alkali metal salt, an alkaline earth metal salt, an ammonium salt, an organic base salt, and an organic acid salt of the compound of Formula (I).

6. A preparation method of the compound of Formula (I) or its pharmaceutically acceptable salt according to claim 1, comprises the following synthetic route:

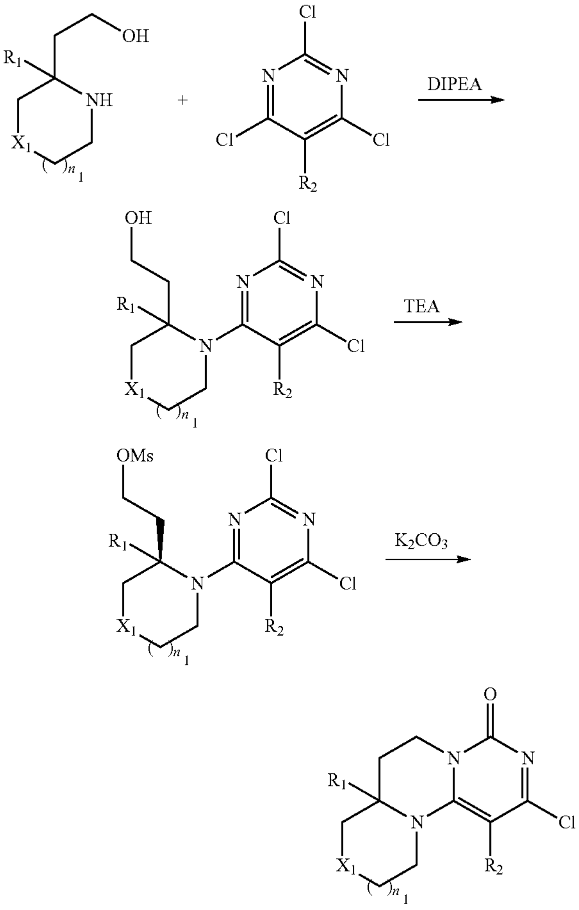

-continued

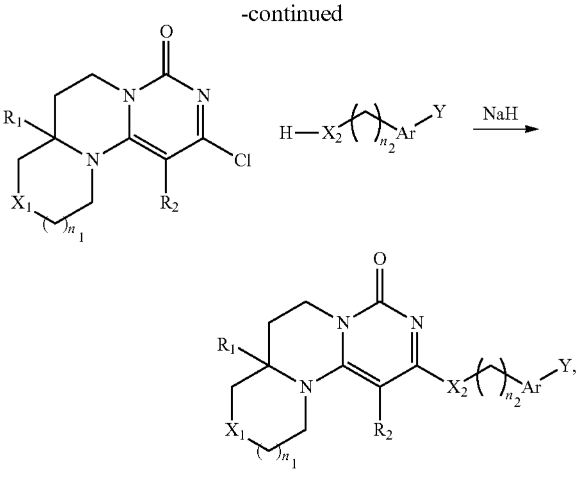

Formula 1 wherein, in the synthetic route, the DIPEA represents N,N-diisopropylethylamine, the TEA represents triethylamine.

7. A pharmaceutical composition comprising an effective amount of the compound of Formula (I) according to claim 1 or a pharmaceutically acceptable salt thereof, and a pharmaceutically acceptable carrier.

8. The compound of Formula (I) or a pharmaceutically acceptable salt thereof according to claim 1, wherein the pharmaceutically acceptable salt is selected from a group consisting of salts formed by the compound of Formula (I) and an organic base, and wherein the organic base is selected from a group consisting of trialkylamine, pyridine, quinoline, piperidine, imidazole, picoline, dimethylaminopyridine, dimethylaniline, N-alkylmorpholine, 1,5-diazabicyclo[4.3.0]nonene-5, 1,8-diazabicyclo[5.4.0]undecene-7, and 1,4-diazabicyclo[2.2.2]octane;

or the pharmaceutically acceptable salt is selected from a group consisting of salts formed by the compound of Formula (I) and an acid, wherein the acid is selected from a group consisting of hydrochloric acid, hydrobromic acid, hydroiodic acid, sulfuric acid, nitric acid, phosphoric acid, or carbonic acid, formic acid, acetic acid, propionic acid, oxalic acid, malonic acid, succinic acid, fumaric acid, maleic acid, lactic acid, malic acid, citric acid, citric acid, tartaric acid, carbonic acid, picric acid, methanesulfonic acid, ethanesulfonic acid, p-toluenesulfonic acid, glutamic acid, and pamoic acid.

9. The pharmaceutical composition according to claim 7, wherein the pharmaceutical composition is in a dosage form selected from a group consisting of oral formulations, rectal formulations, and parenteral formulations.

10. The pharmaceutical composition according to claim 9, wherein the dosage form is selected from a group consisting of solid formulation, liquid formulation, tablet, powder, granule, capsule, aqueous oily suspension, syrup, solution for injection, aqueous and oily suspension.

11. The compound or a salt thereof according to claim 2, wherein the compound represented by the Formula (I) is a tautomer, a mesomer, a racemate, an enantiomer, a diastereoisomer, or a mixture thereof.

* * * * *